(12) United States Patent
Peters et al.

(10) Patent No.: US 8,298,167 B2
(45) Date of Patent: Oct. 30, 2012

(54) MODULAR HEMOFILTRATION APPARATUS WITH INTERACTIVE OPERATOR INSTRUCTIONS AND CONTROL SYSTEM

(75) Inventors: Harold Peters, Snow Hill, NC (US); Adam Heintzelman, Oakland, CA (US); Jacob Kearns, El Sobrante, CA (US); Tommy Cooper, Friendswood, TX (US); Michael Delmage, Napa, CA (US)

(73) Assignee: B. Braun Avitum AG, Melsungen (DE)

( * ) Notice: Subject to any disclaimer, the term of this patent is extended or adjusted under 35 U.S.C. 154(b) by 348 days.

(21) Appl. No.: 12/608,806

(22) Filed: Oct. 29, 2009

(65) Prior Publication Data
US 2010/0121246 A1    May 13, 2010

Related U.S. Application Data

(60) Provisional application No. 61/110,852, filed on Nov. 3, 2008.

(51) Int. Cl.
*A61M 37/00* (2006.01)
*C02F 1/44* (2006.01)

(52) U.S. Cl. ............... 604/5.04; 604/6.09; 604/6.11; 604/6.16; 210/645; 210/646

(58) Field of Classification Search ............. 604/5.01, 604/5.04, 6.01, 6.09, 6.11; 210/645, 646, 210/739
See application file for complete search history.

(56) References Cited

U.S. PATENT DOCUMENTS

| | | | |
|---|---|---|---|
| 5,036,909 | A | 8/1991 | Whitehead et al. |
| 5,605,627 | A | 2/1997 | Carlsen et al. |
| 5,910,252 | A | 6/1999 | Truitt et al. |
| 6,200,485 | B1 | 3/2001 | Kitaevich et al. |
| 6,613,009 | B1 | 9/2003 | Bainbridge et al. |
| 6,849,183 | B2 | 2/2005 | Gorsuch et al. |
| 2009/0084717 | A1 | 4/2009 | Delmage et al. |
| 2010/0089806 | A1 | 4/2010 | Peters et al. |
| 2010/0094192 | A1 | 4/2010 | Peters et al. |
| 2010/0094194 | A1 | 4/2010 | Peters et al. |

OTHER PUBLICATIONS

Search Report and Written Opinion for International Application No. PCT/US2009/63004 filed Nov. 2, 2009.
Sueoka, Akinori, Present Status of Apheresis Technologies: Part 2. Membrane Plasma Fractionator, *Therapeutic Apheresis*, vol. 1, No. 2, May 1997, pp. 135-146.

*Primary Examiner* — Leslie Deak
(74) *Attorney, Agent, or Firm* — RatnerPrestia

(57) ABSTRACT

An apparatus for carrying out selected fluid management and/or renal replacement patient therapy is characterized by an interactive operator control system having operator inputs for selectively changing a panel kit, replacing a filter cartridge, and/or changing to a different patient therapy during a currently running patient therapy, and providing operator instructions for carrying out tasks for completing same. In one embodiment, the interactive operator control system is also characterized by automatically serially identifying different setup steps to be carried out during system setup, displaying the successive steps substantially throughout the system setup as well as displaying on the operator interface screen sequential tasks to be carried out for each of the different setup steps.

29 Claims, 26 Drawing Sheets

CVVHD

FLOW RATES

SETUP

RUN / PAUSE

| | | Rx %WFR 0.0 | | | |
|---|---|---|---|---|---|
| BLOOD | REPLACEMENT FLUID | DIALYSATE | EFFLUENT | NET REMOVAL | THREE HOUR EXCESS FLUID LIMIT |
| 120 | 0 | 1000 | 200 | 250 | |
| 0 - 200 mL/min | 0 - 4500 mL/hr | 0 - 4500 mL/hr | 0 - 4500 mL/hr | 0 - 4500 mL/hr | 140 - 400 mL | mL/hr/kg 35.0

ENTER

FLOW RATES | PATIENT INFO | ALARM LIMITS | TIME DATE

STATUS | SETUP | ALARMS | MODIFY | HISTORY

FIG. 14A

MODULAR HEMOFILTRATION APPARATUS WITH INTERACTIVE OPERATOR INSTRUCTIONS AND CONTROL SYSTEM

CROSS-REFERENCE TO RELATED APPLICATIONS

This application claims priority to U.S. Provisional Patent Application No. 61/110,852 filed Nov. 3, 2008 and incorporated herein by reference.

BACKGROUND OF THE INVENTION

Hemodialysis systems have been designed to carry out blood therapy procedures such as slow continuous ultrafiltration (SCUF), continuous veno-venous hemofiltration (CVVH), continuous veno-venous hemodialysis (CVVHD) or continuous veno-venous hemodiafiltration (CVVHDF). These continuous renal replacement therapies, referred to as CRRT, are designed for removal of metabolic waste and excess fluid from patients in fluid overload and who need renal support. Presently available extracorporeal blood treatment apparatus often requires inconvenient and time consuming setup procedures including cleaning and/or replacing the blood and/or fluid tubing for different patients and for different therapies. Such procedures may require the apparatus to be removed from a patient's bedside or room to another location, or replacing an apparatus with a system that is set up and configured for carrying out a specific therapy.

U.S. Pat. No. 5,910,252 describes an apparatus configured for performing the different blood therapies and provides means for selecting one of the therapies to be carried out. The described apparatus is an assembly of all pumps, tubing, multiple fluid supply reservoirs, waste fluid container and filter cartridge necessary for performing any one of the selected blood therapies.

U.S. Pat. No. 6,200,485 describes another multipurpose hemofiltration system comprising an assembly of a blood filter cartridge, pumps, fluid reservoir and waste fluid container, components for comparing the weights of the fluid reservoir and waste fluid container and means for controlling the pump operations and rate in response to the compared weights during the therapy.

A Prismaflex™ system marketed by Gambro of Lakewood, Colo. offers selection of different CRRT therapies. The system allows the user to select a prepackaged, preassembled assembly incorporating all of the components including specific column and type of filter membrane or membrane filter surface area and all preconnected tubing for carrying out the selected therapy.

In U.S. patent application Ser. No. 12/183,537, filed Jul. 31, 2008 (TRANSVI.024A), there is described a modular hemofilter apparatus having removable panels for multiple and alternate blood therapy. The apparatus and system described in the aforesaid application provides a flexible treatment system characterized by a panel assembly having removable and disposable panels installed on the apparatus housing control unit whereby filter columns and/or tubing sets mounted on the panels may be replaced with filters and/or panels having different tubing configurations to accommodate different blood treatment therapies. The aforesaid application is incorporated herein by reference in its entirety.

In U.S. Provisional Patent Application No. 61/105,703 filed Oct. 15, 2008 (TRANSVI.025PR), the aforesaid modular hemofiltration apparatus with removable panels is further described including special and unique panel designs and tubing configurations. In U.S. Provisional Patent Application No. 61/105,712 filed Oct. 15, 2008 (TRANSVI.026PR), there are disclosed components and features for readily and efficiently manually mounting and removing the panels and filter cartridges by an operator. The aforesaid provisional applications are incorporated herein by reference in their entireties, respectively.

SUMMARY OF THE INVENTION

The apparatus described herein comprises a control unit with blood and fluid pumps, a manually installed replaceable panel kit mounted on the control unit having blood and fluid supply tubing on the panels, a replaceable filter cartridge, a controller CPU configured for operating the system including blood pump and fluid pumps and an interactive operator control system with an operator interface screen operatively connected to the controller. The controller CPU comprises one or more microprocessors provided with software configured to operate the apparatus in response to operator input selections and provide apparatus operating instructions and status of selected therapy parameters. The interactive operator control system is characterized by operator inputs for selecting a CRRT patient therapy, changing the panel kit, replacing the filter cartridge and changing to a different patient therapy from a currently running patient therapy without changing the panels or the filter cartridge. The operator input control panel also provides step-by-step operator instructions for changing the panel kit, replacing a filter cartridge and changing patient therapy during a running patient therapy. The interactive user control system utilizes an operator interface touch-screen with graphic controls whereby the operator may select system operations and is provided with instructions for carrying out the selected system operations and patient therapy sessions. The system also provides operator selection of temporary patient disconnect and later start procedure during a current selected therapy session as well as detailed operator instructions for carrying out the procedures. In another embodiment, the operator control system is characterized by a setup procedure including automatically serially identifying different setup steps during the system setup with the setup steps displayed substantially throughout the setup with the operator interface screen displaying sequential tasks to be carried out by the operator for the setup step currently being carried out. These as well as other components, features, parameters and advantages of the apparatus and its use will be further evident from the following detailed description.

BRIEF DESCRIPTION OF THE DRAWINGS

FIGS. 14A-14C illustrate fluid flow and alarm adjustment screens.

DETAILED DESCRIPTION OF EMBODIMENTS

Figure 1:
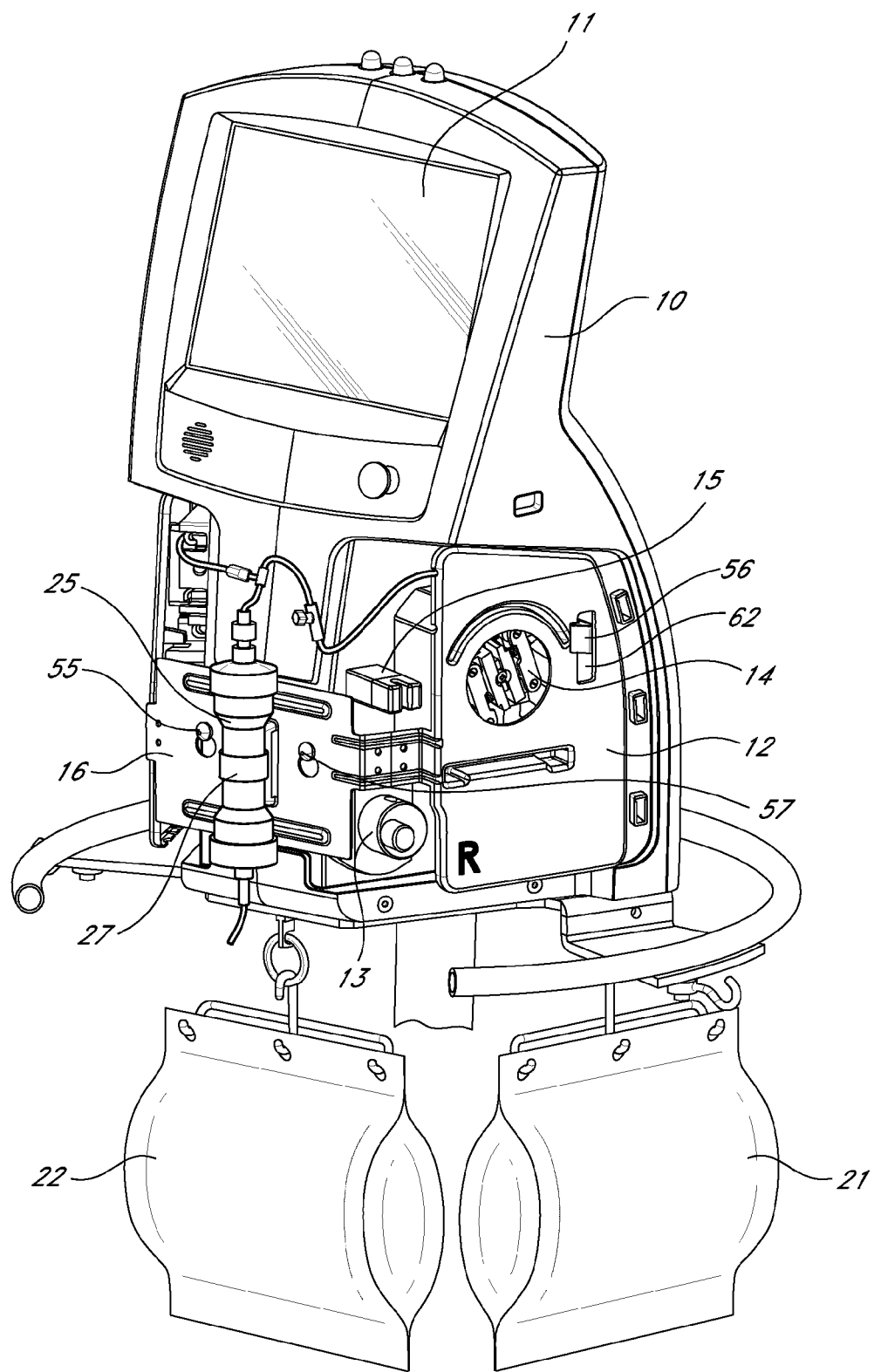
FIGS. 1 and 2 are perspective views of the hemofiltration control apparatus showing the front and different sides of the panel assembly mounted on the control unit housing.
Figure 2:
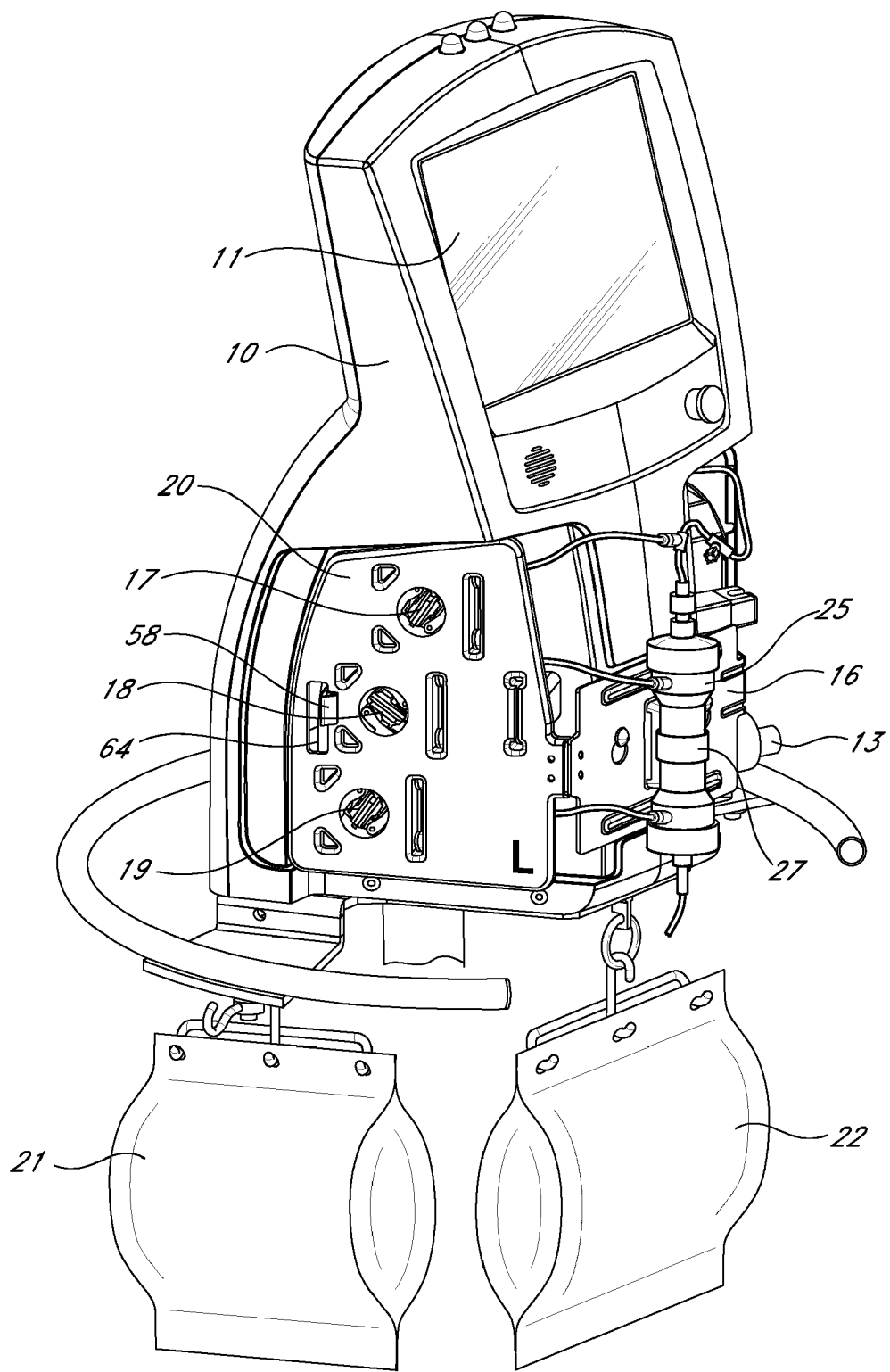

FIGS. 1 and 2 show the hemofiltration assembly including the control unit housing 10 with an operator interface touchscreen 11, illustrating opposite side views from the front corners of the apparatus. In FIG. 1, the blood side is shown with blood pump rotor 14 viewable through an opening in blood panel 12. In FIG. 2, three fluid pump rotors 17, 18, 19 are visible through viewing ports in fluid panel 20. On the front, a filter cartridge panel 16 with mounted hemofilter 25 is shown. The hemofilter, which is removable, is secured on the front panel with a filter cartridge strap 27 threaded through slots in the front panel. The strap may be conveniently provided with contact-type, adjustable securing components such as hook and loop (Velcro®) components which readily provide for securing different sized filter cartridges. Alternatively, the contact surfaces of the hemofilter and front panel may be provided with contact attaching means. The panels of the panel assembly set are mounted on the control unit housing by features and components as will be explained further hereinafter. In FIG. 1, a air detector 15 and return line clamp 13 are shown, and in FIGS. 1 and 2 fluid holding bags 21, 22, 23 are also shown.

Figure 3:
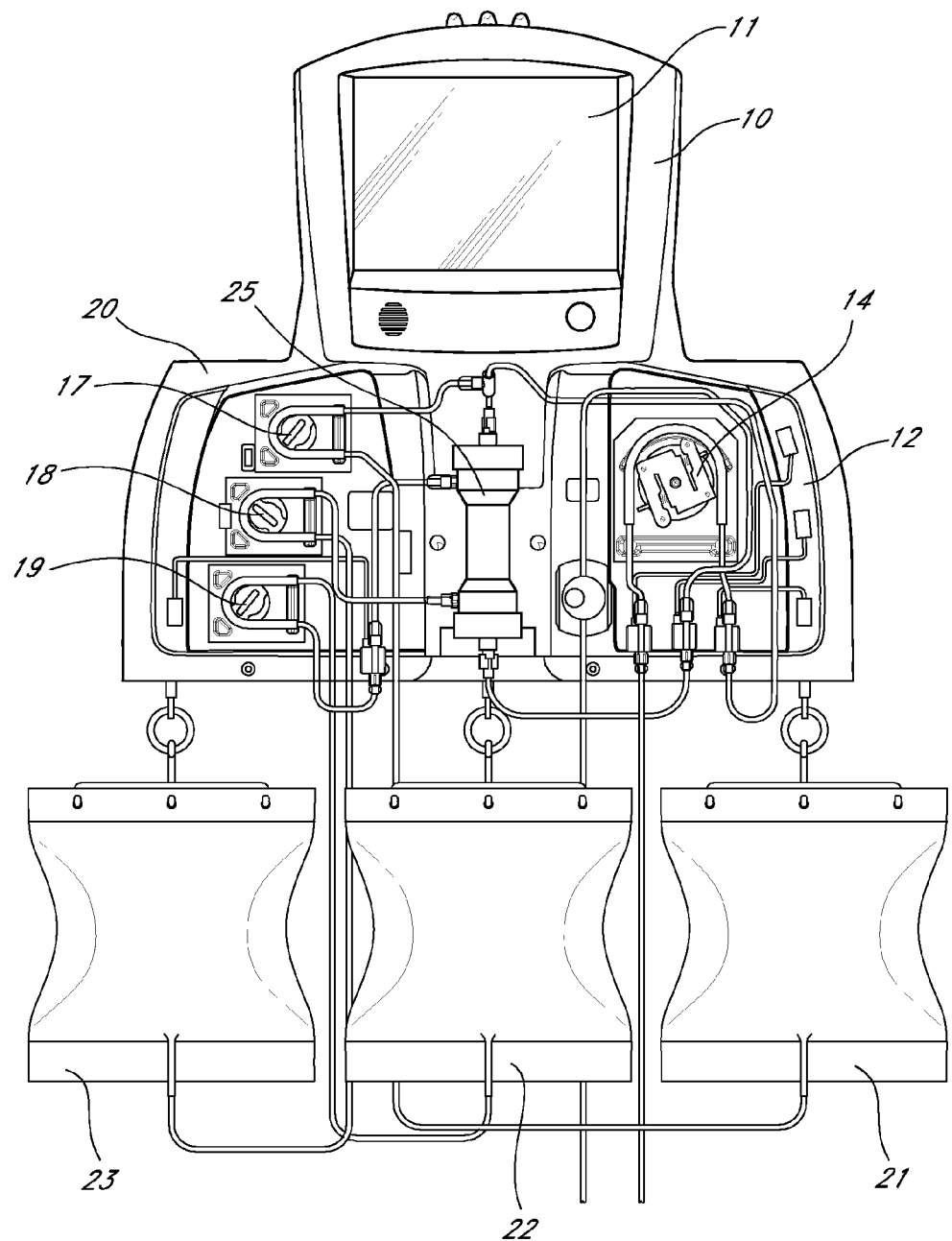
FIG. 3 is a schematic view of the modular blood therapy apparatus showing the interior panel fluid and blood tubing layout design with three fluid holding bags in fluid communication with the tubing.
Figure 4:
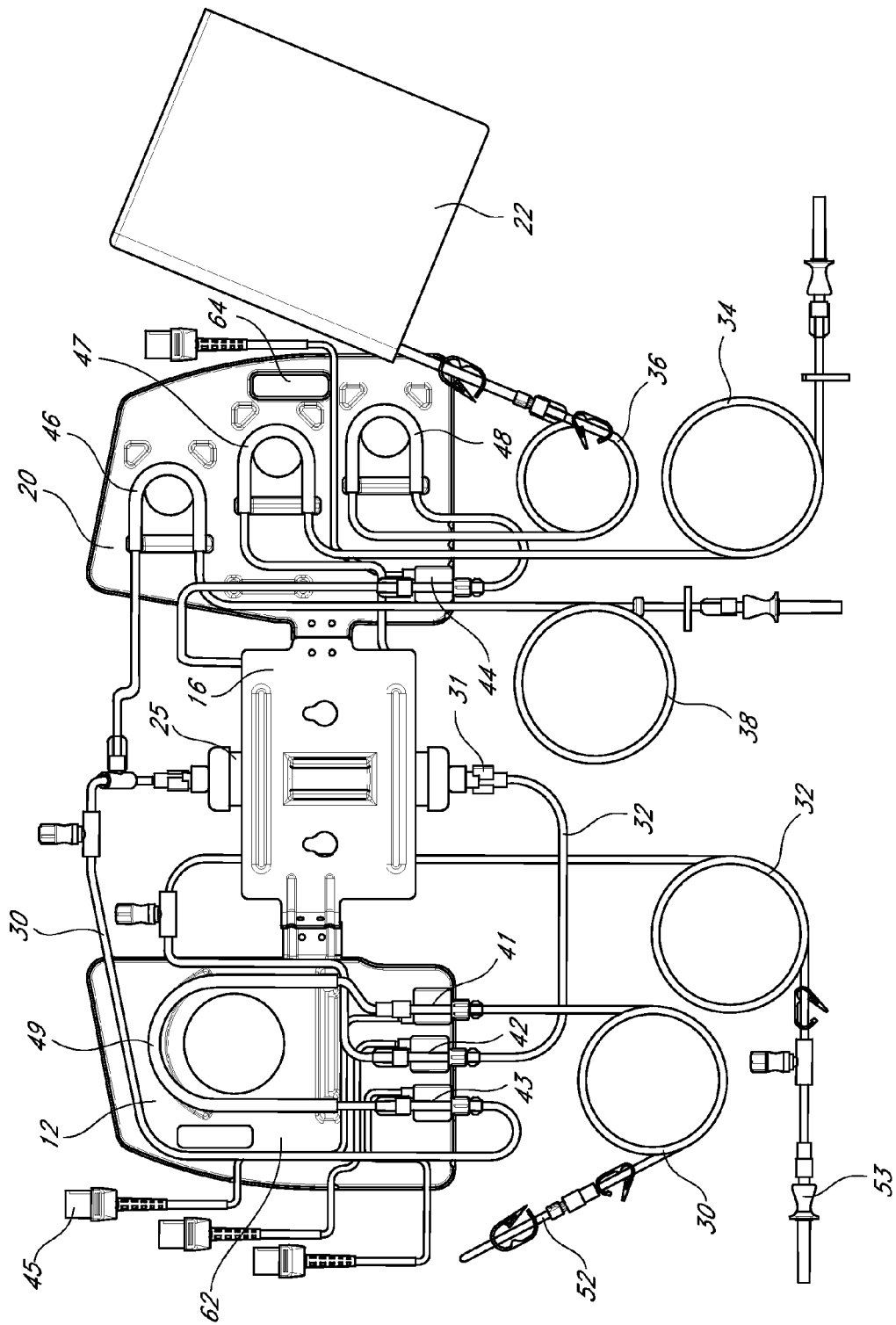
FIG. 4 shows the interior panel surfaces with mounted tubing on blood supply and fluid tubing panels and a connected center panel and mounted hemofilter cartridge.

In FIGS. 3 and 4 there is shown the interior of the three-panel set with a tubing mounted on or adjacent to the interior panel surfaces and the relationship of the tubing as it is positioned for engagement with the respective blood pump and fluid pumps. Connections between sections or segments of the tubing with one another, with the filter cartridge, fluid pressure transducers, fluid supply containers and an effluent bag as well as to cannulae or catheters for directing blood to or from a patient are also shown.

The blood panel 12 includes blood supply tubing mounted along the interior, generally flat surface of the panel. An arched, upwardly slanted U-shape bend 49 of the blood supply tubing engages the rotors of blood pump 14 when the blood panel is securely mounted on the control unit housing. On the blood panel are positioned three pressure transducers 41, 42, 43 through which different sections of the blood supply tubing channels pass. The end of blood inlet line 30 is attached to a patient access device such as a needle cannula or catheter assembly 52 and includes a clamp for closing off the blood supply tubing. A blood pump 14 (FIGS. 1, 3) pumps blood along blood supply tubing blood inlet line 30 from the patient to the filter cartridge 25 via a blood inlet adapter 29. A blood return line 32 secured to an opposite end of the filter cartridge via a blood return adapter 31 includes segments directing the return line through the pressure transducer 42 and to a needle cannula assembly and/or catheter 53. Each of the pressure transducers has a pressure signal cable attached to a transducer plug 45, to be inserted in a socket on the control unit housing and for monitoring pressure signals from the respective pressure transducers along the blood inlet and return line segments.

The fluid side of the assembly comprises fluid panel 20 with tubing mounted along the generally flat interior surface. The fluid tubing is configured and shaped to engage three fluid pumps 17, 18, 19 secured to the control unit. Similar to the configuration of the blood supply tubing, three arched or U-shaped tubing segments 46, 47, 48 are provided to engage the rotors of the respective fluid pumps for driving fluids through the tubing. The different tubing segments and cooperating fluid pumps direct dialysate fluid, replacement fluid, saline/anticoagulant fluid, depending on the apparatus and blood treatment configuration, and effluent or waste fluid from the filter to the effluent container or bag. More specifically, replacement fluid line 38 directs replacement fluid from replacement fluid bag 21 via arched tubing section 46 to blood inlet line 30 and into the upper end of the filter cartridge 25. A second fluid tubing line 34 directs dialysate fluid from dialysate fluid bag 23 into the side of the filter cartridge 25 via arched tubing section 47. A third fluid tubing section directs waste effluent from the filter cartridge to effluent fluid collection bag 22 via arched tubing section 48. A pressure transducer 44 is also positioned on the fluid panel. In a preferred embodiment, all of the pressure transducers are positioned on the respective panels such that when the panels are securely mounted on the control unit housing, the pressure transducers are at the same vertical elevation so that accurate pressure readings can be taken and compared, without further adjustment, which would otherwise be required to compensate for differences in transducer elevations. More specific and detailed descriptions of the tubing layouts on the respective blood and fluid panels are described and shown in aforesaid U.S. patent application Ser. No. 12/183,527 (TRANSVI.024A) and U.S. Provisional Application No. 61/105,703 (TRANSVI.025PR).

The three-panel kit is manually mounted on the control unit housing with panel engaging and tensioning clips attached to the housing frame. Observing FIGS. 1 and 2, panel mounting clips 56, 58 on respective sides of the control unit housing are spring biased for extending through aperture slots 62, 64 on the respective blood and fluid panels and which apertures are to be aligned with the mounting clips (see FIGS. 1, 2, 4). The clips are shaped to provide a slanted flange extending through the aperture portion which flange is forced against an edge of the aperture against the spring bias of a clip, loading the spring. The clips are self-engaging and snap into place when the flanges clear the aperture. To remove the side panels, the operator manually forces each spring-loaded clip to the side until it clears and is able to pass through the aperture. The front panel 16 is aligned with two protruding pegs or hangers 55, 57 each of which have an enlarged button or flange at its extremity and a smaller shaft. The apertures on the front panel are shaped with an enlarged aperture port and a narrow aperture slot. When mounting the front panel, an operator aligns the aperture ports with the enlarged pegs, urges the panel against the housing so that the pegs extend through the aperture ports, and the shafts settle into the smaller aperture slots. Thereafter, the operator snaps the blood and fluid panels into the mounting positions via the aforesaid mounting clips which engage the panels in the desired positions. Thus, the panels are easily and efficiently manually mounted and disengaged for removal. A further description of the mounting components and procedure are described in U.S. Provisional Application No. 61/105,712, filed Oct. 15, 2008 (TRANSVI.026PR), the description of which is incorporated herein by reference in its entirety.

Figure 5:
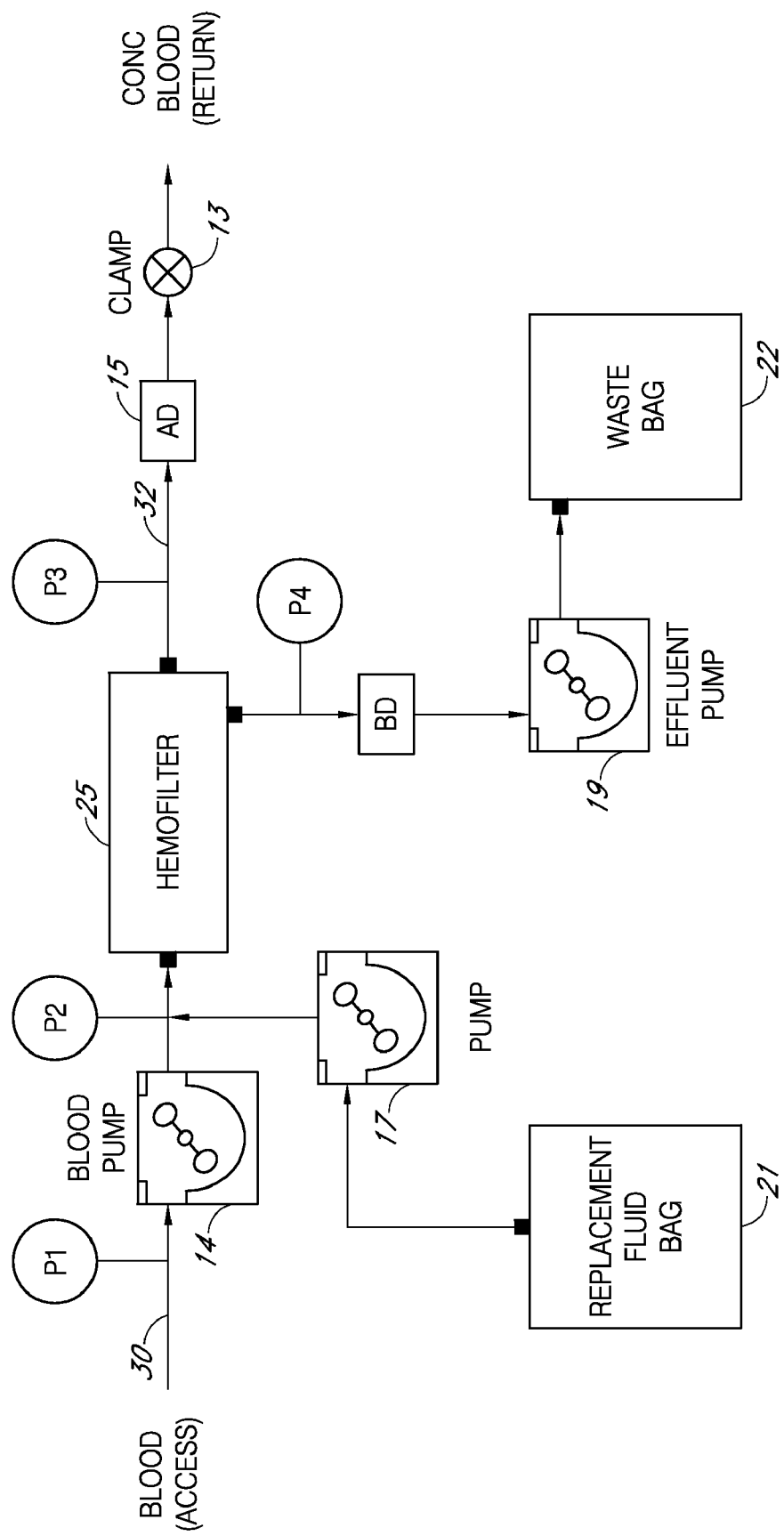
FIGS. 5 and 6 schematically show components of the apparatus configured for carrying out selected CRRT blood filtration therapies.
Figure 6:
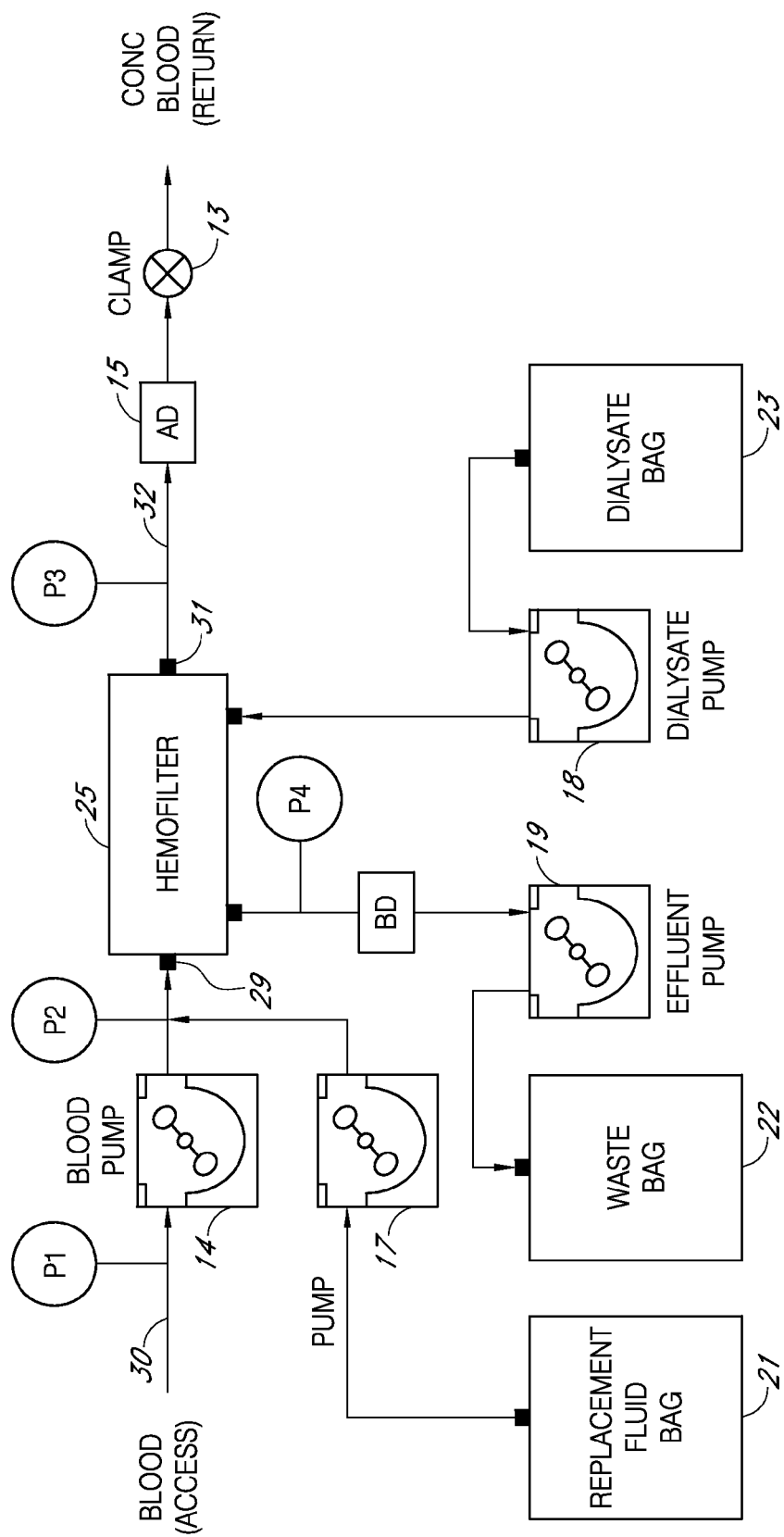

Referring also to FIGS. 5 and 6, the schematic components of the apparatus are illustrated and configured for carrying out the selected CRRT blood therapy procedures as set forth in paragraph [0002]. In FIG. 5, the apparatus configuration is shown for carrying out CVVH to remove solute by convection and fluid removal by ultrafiltration. The hemofilter membrane separates plasma water by ultrafiltration and a replacement fluid from container 21 is pumped into the blood flow path via pump 17. The replacement fluid adds selected solutes lost through convection. The concentration of the undesired solutes is decreased as treatment is carried out and the desired solutes are replaced at concentrations maintained at the appropriate level. The removed solutes are directed to a waste bag 22 via effluent pump 19. The apparatus illustrated in FIG. 5 may be used to carry out SCUF to remove excess patient fluid by ultrafiltration only. For SCUF, no replacement fluid or dialysate is used and the apparatus shown is modified by elimination of the replacement fluid bag 21 and pump 17 is not operated.

The apparatus configuration of FIG. 6 may be used for carrying out CVVHD and CVVHDF. CVVHD removes solute by diffusion and patient fluid removal by ultrafiltration. For CVVHD, no replacement fluid is introduced, the replacement fluid bag 21 may be eliminated and pump 17 is not operated. However, both CVVHD and CVVHDF utilize dialysate fluid which is directed into the hemofilter 25 and undesirable solutes flow from the blood through a membrane in the filter and into the dialysate fluid via diffusion. For CVVHDF, replacement fluid is pumped to the blood flow line from replacement fluid bag 21. Replacement fluid may be added to the blood flow upstream from the filter, as shown, or it may be introduced into the patient return flow line downstream from hemofilter 25.

In carrying out the aforesaid therapies, an anticoagulant such as heparin, a citrate or other anticoagulant may be added to the replacement fluid, or it may be introduced into the blood access line from the patient, upstream from the hemofilter, using a syringe, pump or other fluid injection apparatus. Plasma and/or albumen may be also added to the filtered blood to be returned to the patient, again using a suitable fluid injection apparatus component, not shown.

Figure 7:
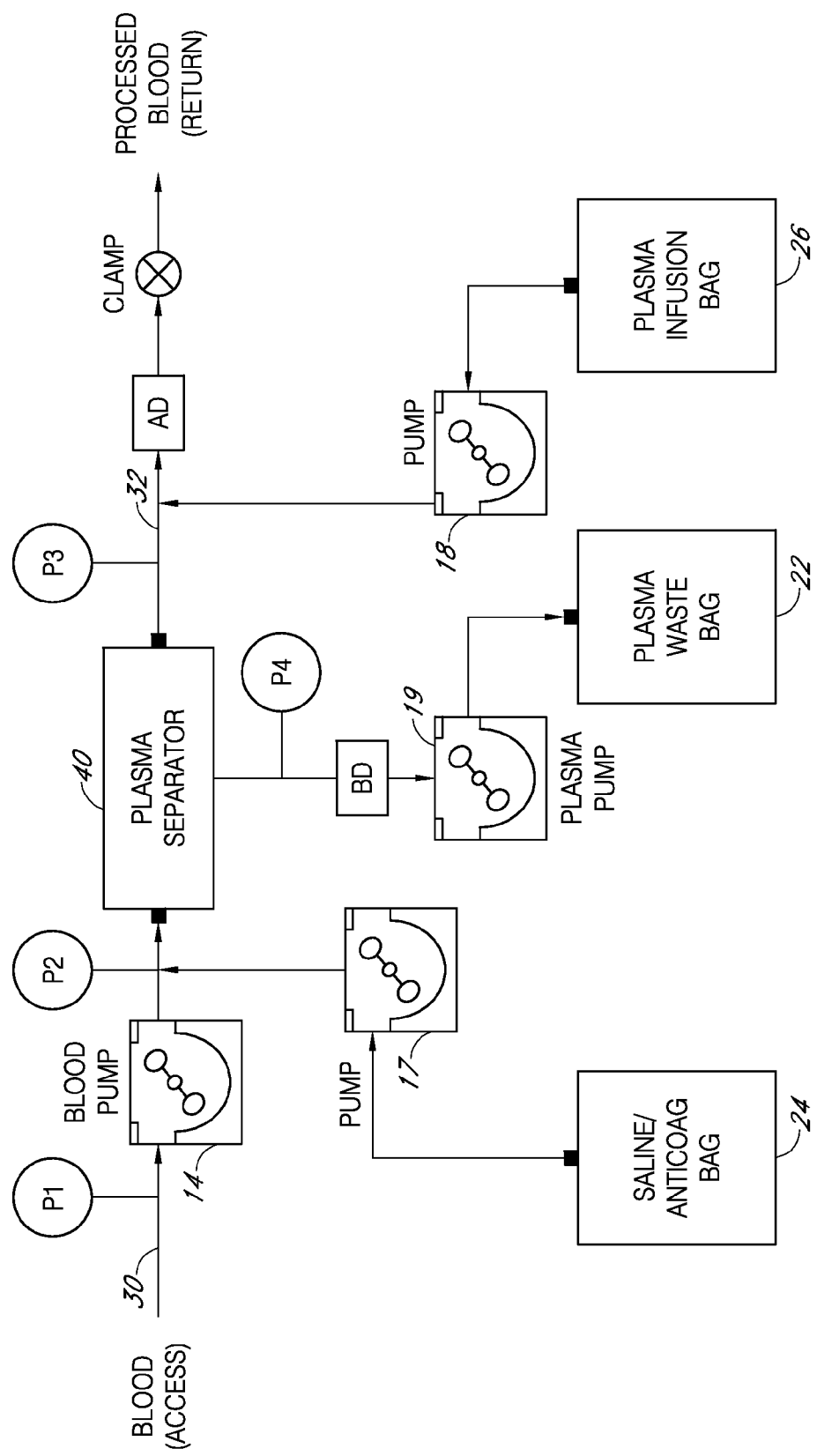
FIGS. 7 and 8 schematically show components of the apparatus for carrying out plasma separation and plasma treatment embodiments.
Figure 8:
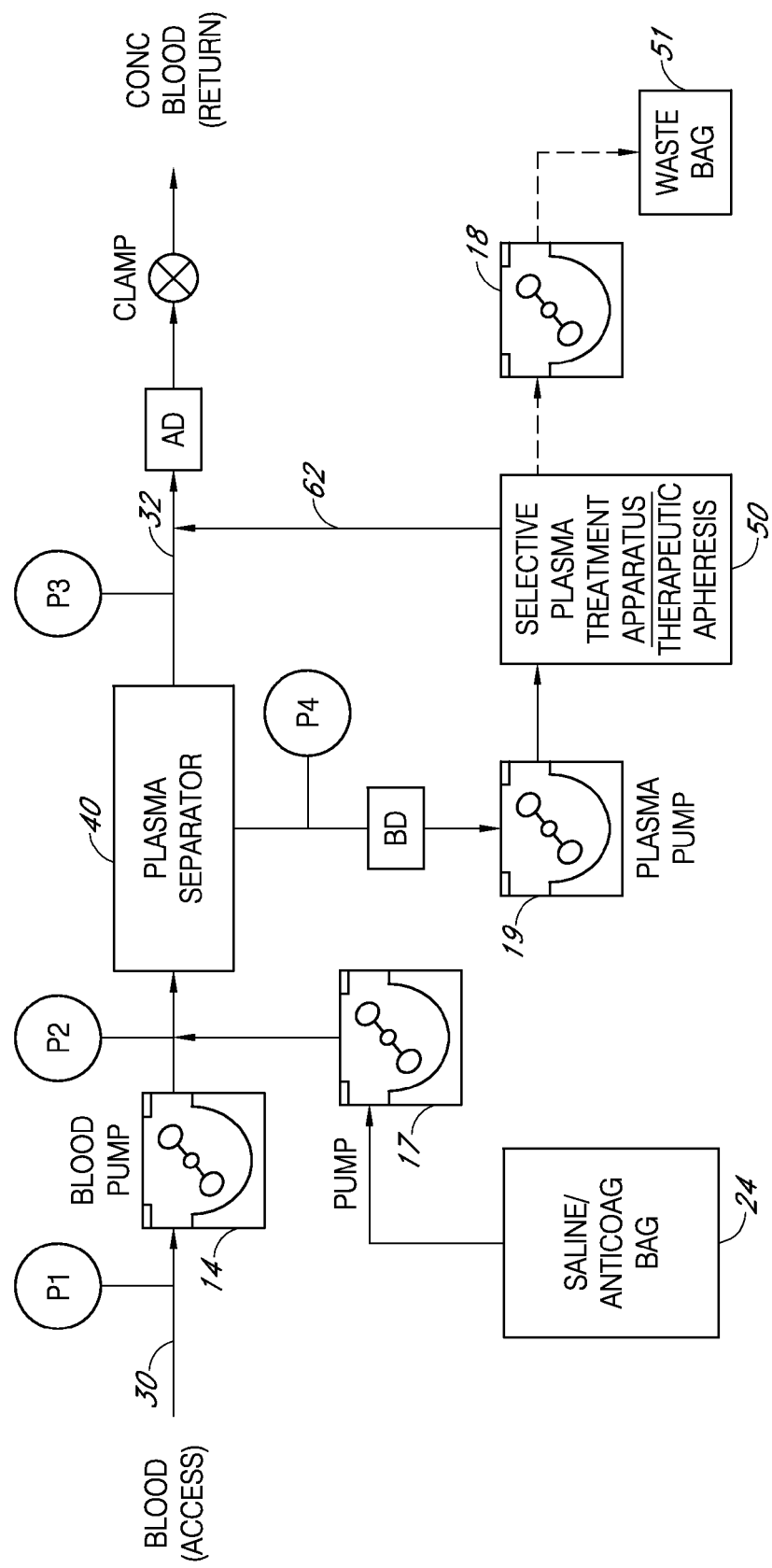

The system and apparatus described herein may be configured to not only carry out four renal replacement therapies and continuous fluid management for continuous renal replacement therapy (CRRT) but also for separating plasma from blood, treating plasma to remove toxins and excess fluid and for therapeutic apheresis as will be described further hereinafter. The apparatus shown in FIGS. 7 and 8 illustrate configurations of the system for carrying out plasma separation, plasmapheresis, plasma exchange, liver support and therapeutic apheresis. In the configurations shown, a plasma separator 40 replaces the hemofilter 25 shown in FIGS. 5 and 6. Plasma is separated from the patient's blood and thereafter discarded and replaced, or the plasma is treated for separation and removal and/or neutralization of selected disease-related components or other poisons, toxins, drugs, etc. In FIG. 7, the system illustrated is configured for carrying out plasma replacement. Blood from the patient is pumped to the plasma separator cartridge 40 which separates plasma across the cartridge membrane. The separated plasma is pumped to a plasma waste bag 22 via pump 19 and replacement plasma from plasma infusion bag 26 is pumped by pump 18. An anticoagulant and saline fluid pump are also shown. Anticoagulant and/or saline solution from bag 24 may be added to the blood at or upstream from the plasma separation cartridge.

FIG. 8 illustrates an embodiment of the apparatus for processing separated plasma for selective plasma treatment. Such selective plasma treatment is referred to as therapeutic apheresis, and includes apparatus capable of selectively removing disease-related components such as toxins, antibodies, proteins, pathogens including bacteria, virus, etc. as well as removing or neutralizing drugs, poisons, or other selected chemical substances. As shown in FIG. 8, a selective plasma treatment apparatus or therapeutic apheresis apparatus 50 is supplied with separated plasma via plasma pump 19 for treating the plasma. Plasma treatment apparatus may include plasma exchange components, centrifugal or membrane-separation filters, cascade or multiple filtration membranes and columns, one or more absorption cartridges capable of absorbing specific disease-related components or drugs, and activated charcoal cartridges. Other examples of selective component removal apparatus include specialized columns incorporating compositions such as cross-linked polyvinyl alcohol gel beads or microporous cellulose beads for removing specific amino acid ligands and antibodies, components capable of chemically processing the plasma to precipitate heparin, salt-amino acids, or for effectively neutralizing drugs, poisons or disease-related components in the plasma. The apparatus may be used for liver support functions as well. Moreover, the selective plasma treatment apparatus may combine different plasma treatment components used in series or parallel for simultaneously or concurrently carrying out multiple plasma treatment or therapy. The treated plasma is directed to the patient via line 33 connected to patient blood return line 32. If needed, the apparatus may be configured with a fourth fluid pump for pumping the treated plasma to the patient return line or to an effluent container. A supplemental fluid pump 18 is shown for directing waste fluid from the selective plasma treatment apparatus 50 to a waste bag 51. Additional description of selective component removal apparatus and technologies are described in U.S. Pat. No. 6,849,183, the relevant portions of which are incorporated herein by reference, as well as in Therapeutic Apheresis, Vol. 1, No. 2, May 1997, pages 135-146. Other examples of such cartridges or plasma exchange components, filters, etc. are disclosed in U.S. Pat. No. 5,605,627, the relevant portions of which are incorporated herein by reference. The selective plasma treatment apparatus may be designed to allow an operator to exchange, replace or modify the configuration of the filters, columns, cartridges, etc. in order to accomplish different plasma treatments on a patient, if desired.

One characteristic of embodiments of the apparatus and system described herein is in the interactive operator control feature. This feature can include an operator interface that provides apparatus operating instructions and therapy status and parameters. In the embodiment described below, the interface is a touch-screen interface. However, other well known interfaces, such as those that use conventional buttons or switches are also contemplated.

As used herein, an input device can be, for example, a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

As used herein, instructions refer to computer-implemented steps for processing information in the system. Instructions can be implemented in software, firmware or hardware and include any type of programmed step undertaken by components of the system.

A Local Area Network (LAN) or Wide Area Network (WAN) may be a corporate computing network, including access to the Internet, to which computers and computing devices comprising the system are connected. In one embodiment, the LAN conforms to the Transmission Control Protocol/Internet Protocol (TCP/IP) industry standard.

As used herein, media refers to images, sounds, video or any other multimedia type data that is entered into the system.

A microprocessor may be any conventional general purpose single- or multi-chip microprocessor such as a Pentium® processor, a Pentium® Pro processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

The system is comprised of various modules as discussed in detail below. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be used in connection with various operating systems such as LINUX, UNIX or MICROSOFT WINDOWS®.

The system may be written in any conventional programming language such as C, C++, BASIC, Pascal, or Java, and ran under a conventional operating system. C, C++, BASIC, Pascal, Java, and FORTRAN are industry standard programming languages for which many commercial compilers can be used to create executable code.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

The operator control system allows an operator to make patient therapy selections and to change patient therapy during a currently running therapy. The interactive operator control system is further characterized by providing step-by-step operator instructions for selectively changing a fluid bag, changing a panel kit, replacing a filter cartridge, temporarily disconnecting a patient and later restarting therapy, all during a current operating or running patient therapy session. The control unit of the apparatus includes a controller linked to software that is configured to provide the aforesaid operating instructions via text or graphical messages appearing on the operator interface screen. An interface module runs on a processor within the apparatus and scans for user input from the touch screen. If the interface module detects user input it runs instructions corresponding to the activated indicators on the touch screen.

FIGS. 9A to 12 illustrate different screens instructing an operator of steps to be carried out for changing a bag, a panel kit, replacing a filter, disconnecting the patient exiting therapy or changing therapy during a currently running therapy. These instructions are accessed by pressing the Operate screen button and then the desired tab.

Figure 9A:
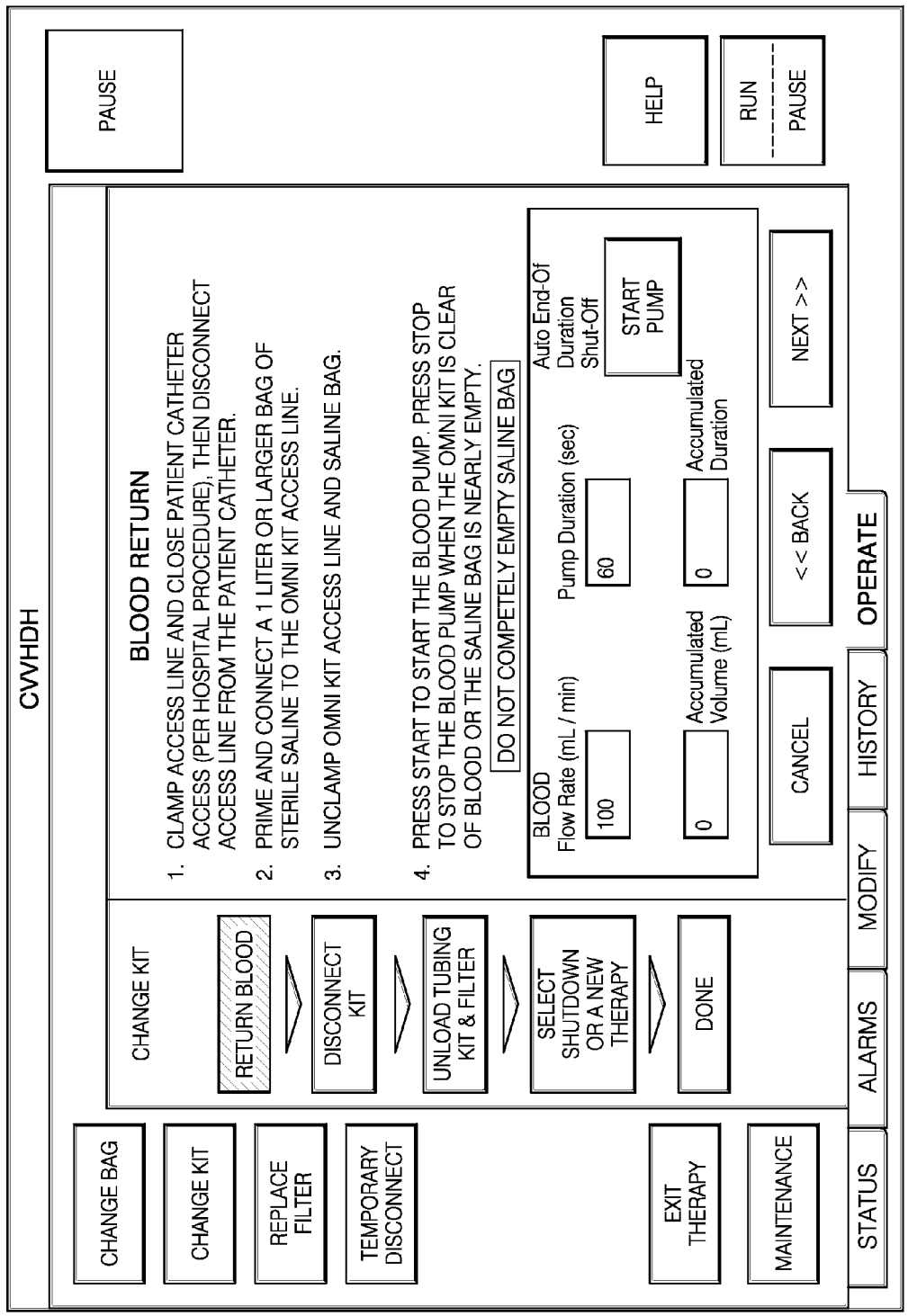
FIGS. 9A and 9B illustrate operator interface screen text message instructions for some steps for changing a panel kit.
Figure 9B:
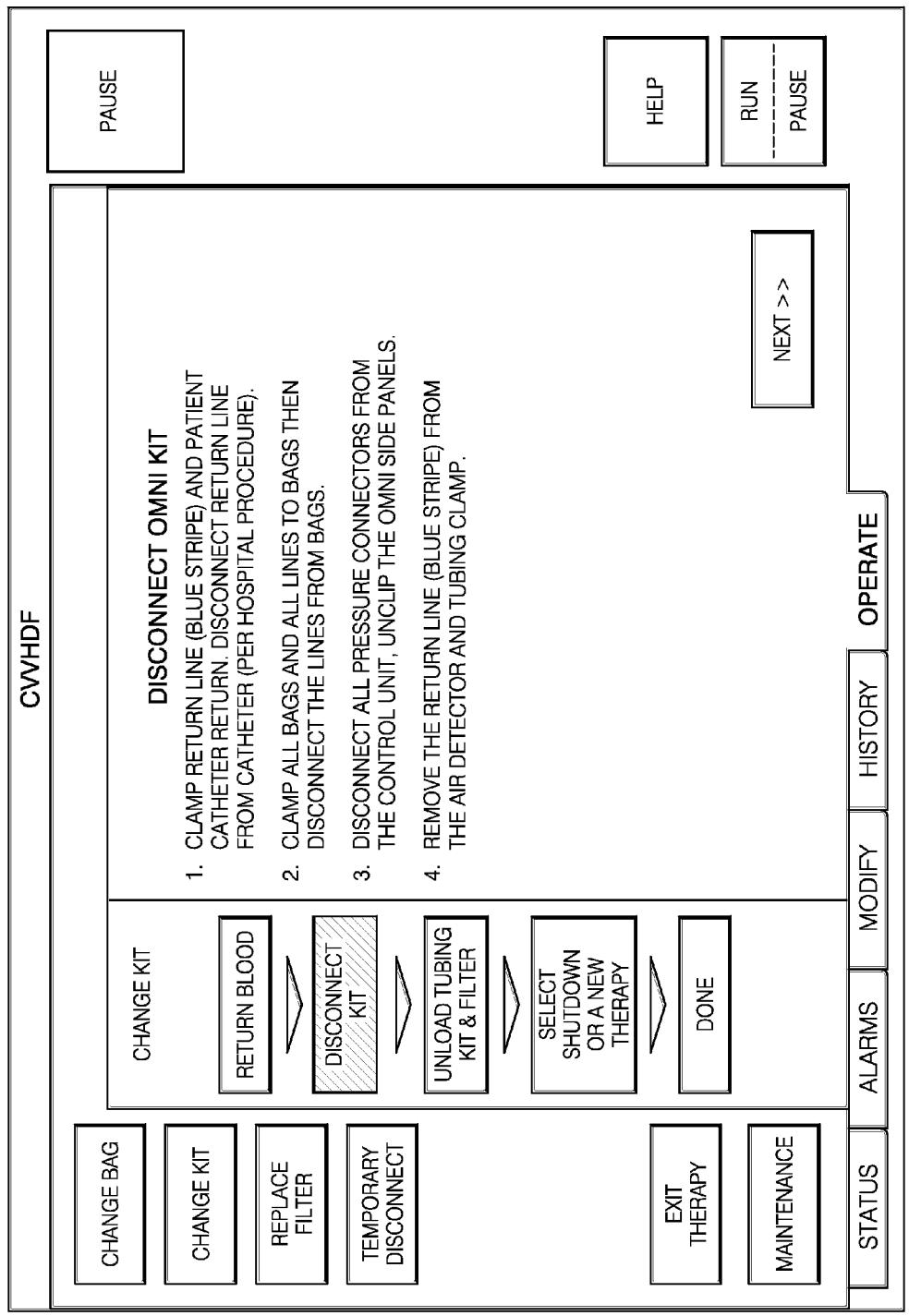

Referring to FIGS. 9A and 9B, there are shown examples of sequential operator interface screens illustrating instructions to an operator for changing a panel kit. The screen illustrated in FIG. 9A includes a "Change Kit" indicator button which an operator can press or activate to provide instructions for changing the panel kit or set, including the filter. In one embodiment, when the Change Kit button has been pressed by an operator an instruction is sent to the controller to stop all the pumps and display the first screen shown in FIG. 9A providing instructions for carrying out the "Blood Return" step. Blood return will not be carried out if clotting is present in the tubing or the filter. The Blood Return step can be skipped by pressing the "Next" tab on the screen.

After blood is returned or skipped, the patient is completely disconnected from the system and the apparatus prepared for panel kit removal according to the instructions shown in FIG. 9B. After disconnecting the panel kit, an operator again presses "Next" and "Kit Unload" screen instructions (not shown) appear. The panel kit is unloaded by pressing "Unload," disengaging the panel clips and pulling on the side panels while the pumps turn. The "Unload" indicator may be pressed multiple times. Panels removed from the system may be disposed of.

Figure 10A:
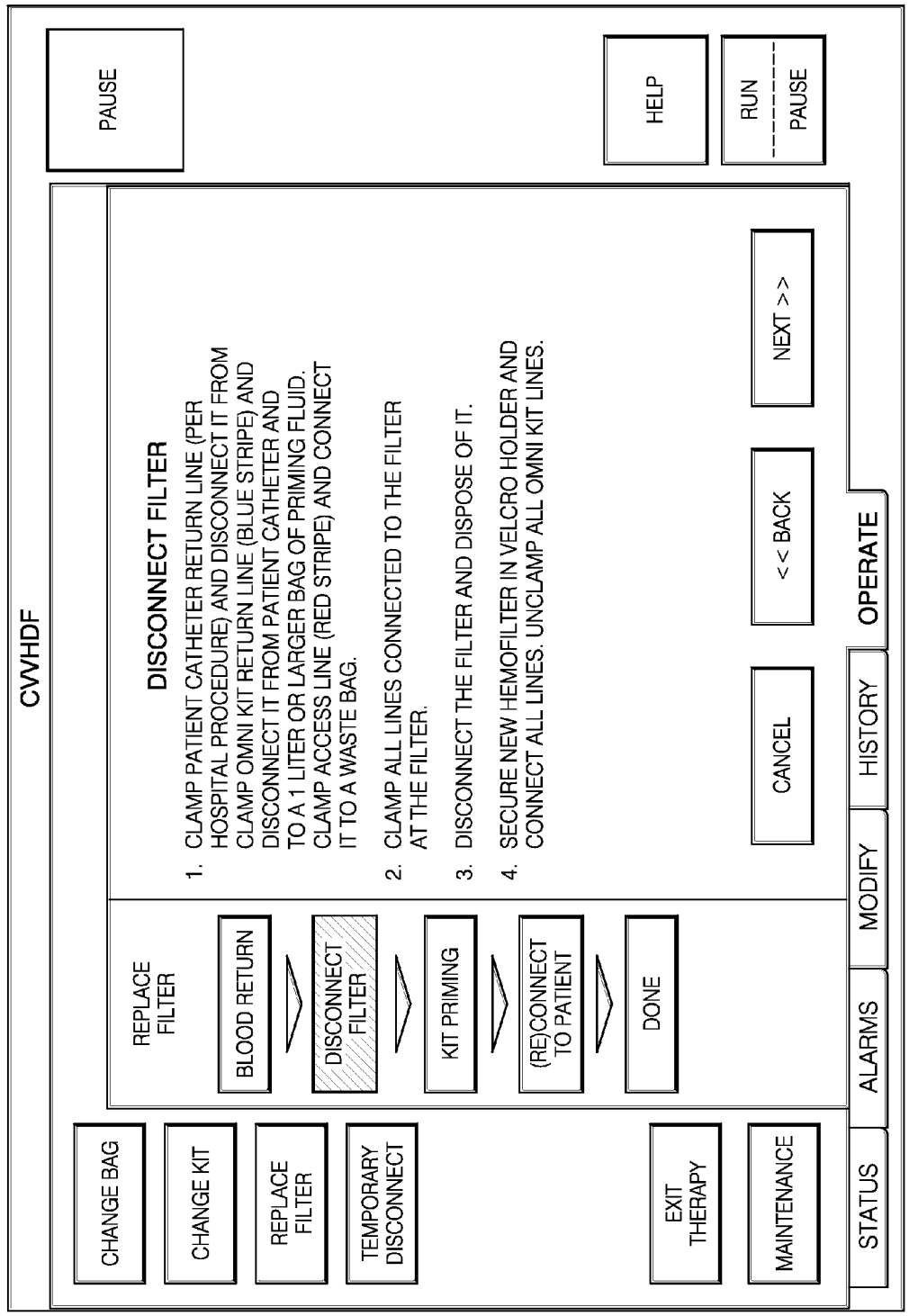
FIGS. 10A and 10B illustrate operator instructions for some steps for replacing a filter cartridge.
Figure 10B:
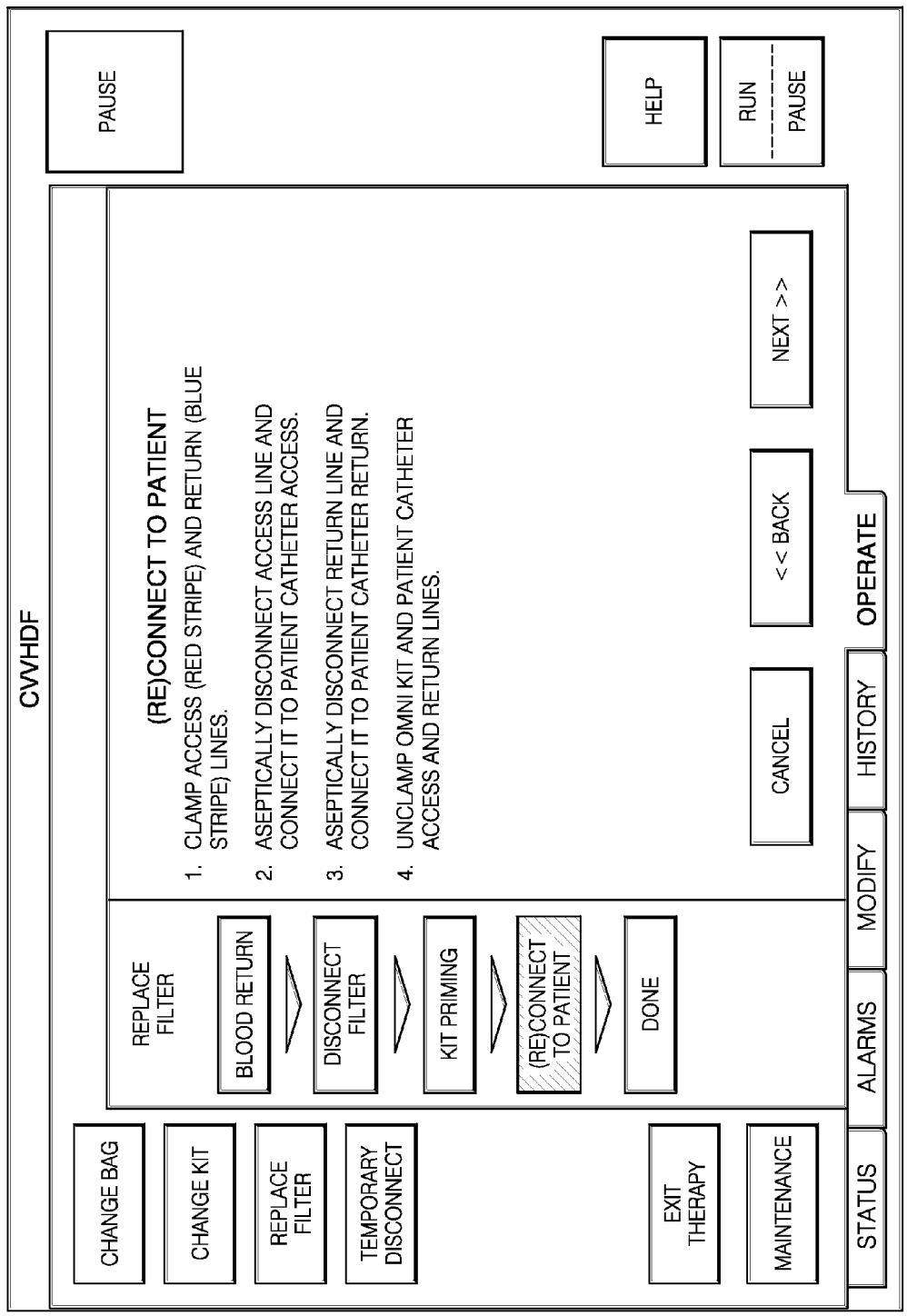

To replace a filter only, without replacing the panel kit, the "Replace Filter" indicator button is touched. All pumps stop and the Blood Return screen of FIG. 9A appears with instructions to guide the operator through a Blood Return step before the old filter is disconnected from the apparatus. Again, if clotting is present in the tubing or filter, the Blood Return step is eliminated. FIG. 10A illustrates screen instructions for disconnecting the patient and removing the old filter. The patient must be disconnected from the system so the new filter can be primed. In disconnecting the old filter, hemostats are used to clamp all the lines connected to the filter. The lines are aseptically disconnected, the old filter removed, the new filter connected and the lines are then unclamped. Thereafter, the operator presses "Next" to advance to a priming step (not shown) and the system is reconnected to the patient following the screen steps shown in FIG. 10B. Once the patient has been connected, the operator presses "Next" and therapy is automatically resumed.

Figure 11:
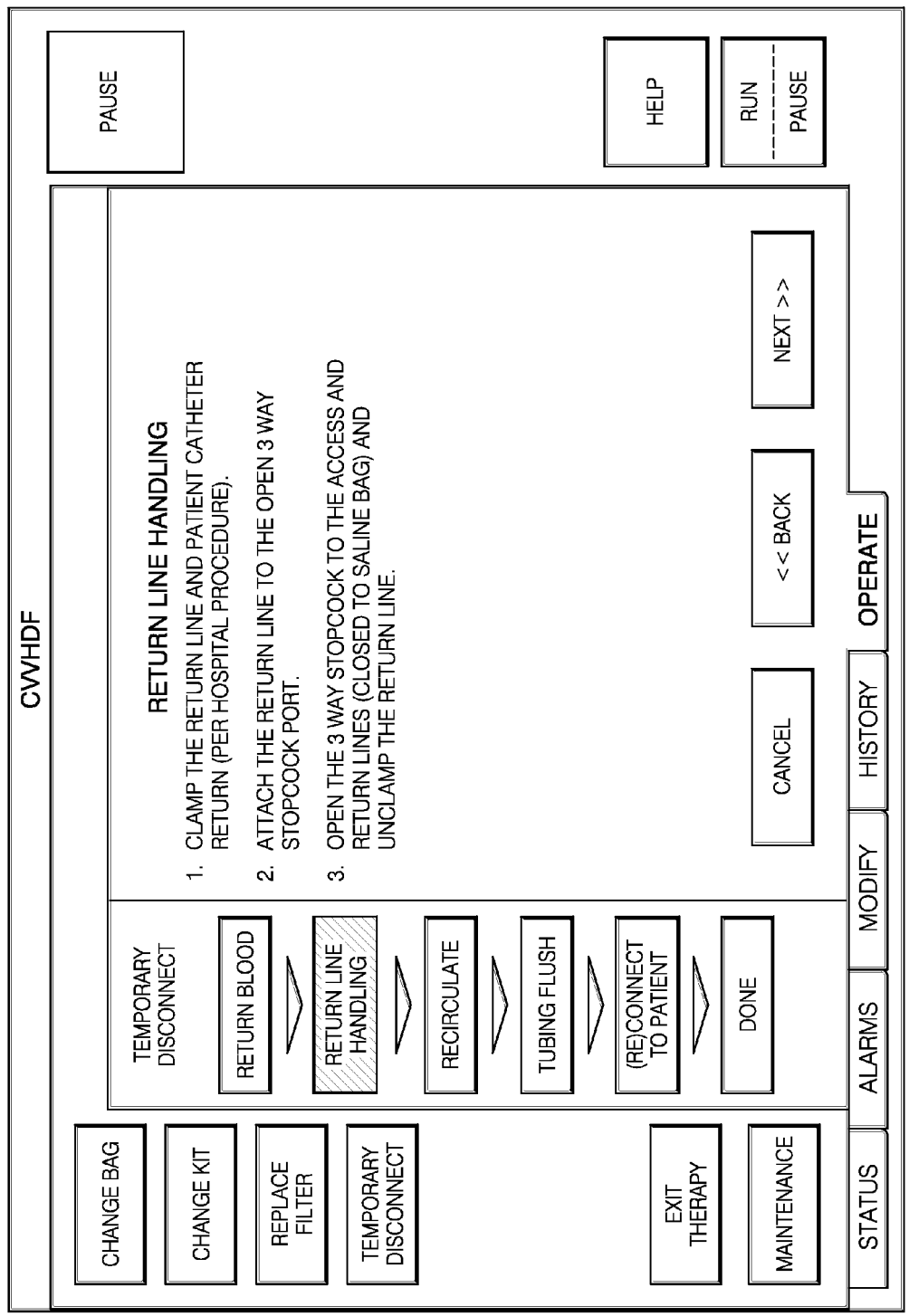
FIG. 11 illustrates one operator instructions screen for temporarily disconnecting a patient during therapy and restarting treatment at a later time.

To disconnect a patient during therapy, the operator may touch the "Temporary Disconnect" indicator button for temporarily disconnecting and restarting treatment at a later time. Once the indicator is pressed, all pumps stop and the "Return Blood" screen shown in FIG. 9A appears. The instructions guide the operator through the Blood Return step before the patient is disconnected as previously described. Return line handling instructions are shown in FIG. 11. The system also provides recirculate and optional flush instructions (not shown). After the optional flush, screen instructions shown in FIG. 10B for reconnecting the patient are automatically presented. After the patient has been reconnected, treatment may be resumed.

Exit therapy is carried out by an operator pressing the "Exit Therapy" indicator located on the operator interface touchscreen. Once the indicator is pressed, all pumps stop and the Blood Return screen shown in FIG. 9A is presented. Again, if clotting is present in the tubing or filter, blood is not to be returned to the patient and a complete patient disconnect from the apparatus is instructed pursuant to the steps shown in FIG. 9B. Thereafter, by pressing the "Next" indicator, the instructions for disconnecting the panel kit and filter are presented pursuant to the steps shown in FIGS. 9B and 10A. The system then allows the operator the choice for exiting or restarting the program.

Figure 12:
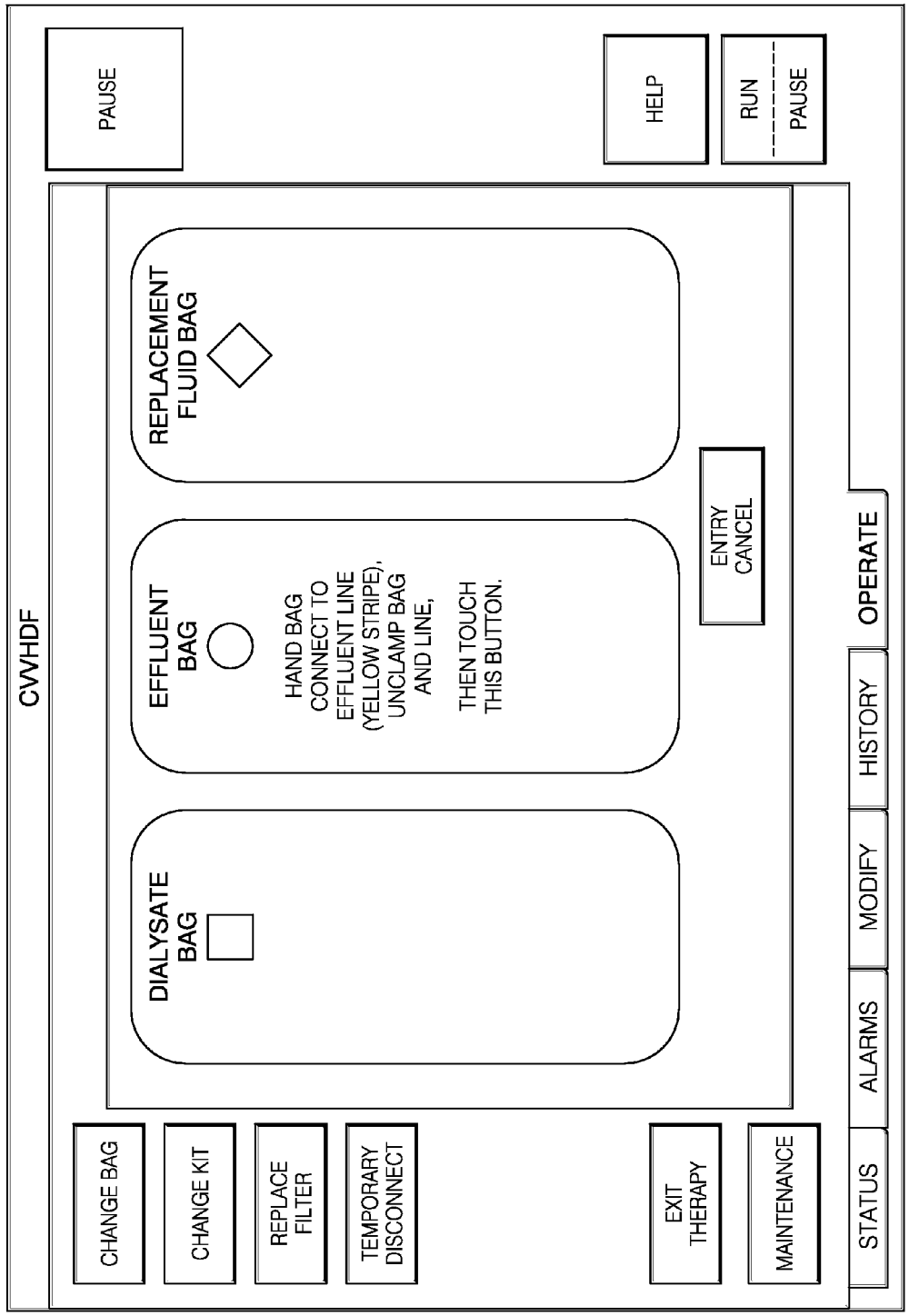
FIG. 12 shows operator instructions for changing a bag.

FIG. 12 shows a "Change Bag" screen that may be accessed for changing a bag during a running therapy. If a bag alarm or warning condition exists, the control system will automatically activate the button for the offending bag. If no alarm condition exists, the button of the bag to be changed may be pressed, or the system will automatically activate the button when the bag is removed from the hook. Once the bag is changed, the fluid line unclamped, and the bag button pressed on the screen, the system automatically resets the alarms and resumes patient treatment.

The aforesaid procedures and steps may be carried out at any time during a running patient therapy. Such aforesaid procedures and steps are accessed during a running therapy by the operator pressing or touching the "Operate" button or tab on the operator interface screen. Such a tab or button is displayed on the screen during the entire running patient therapy treatment. By touching the "Operate" tab or button, the screen will show the different aforesaid procedure including change bag, change kit, replace filter, temporary disconnect and exit therapy as previously described. A presently running therapy may also be stopped and a different therapy started at any time. This may be carried out by the operator touching the "Select Shutdown or a New Therapy" button, see FIG. 9A, whereupon the operator interface screen illustrated in FIG. 13A will appear on the screen allowing the operator to select the new therapy. Again, all sequential screens for each subsequent step to be carried out automatically appear when the operator presses "Next" or other tab indicating completion of the steps shown on the screen.

The operator control system of the present apparatus is further characterized by automatically and serially identifying different setup steps to be carried out by an operator during system setup. Observing FIG. 13A, the different setup steps are shown on the left side of the operator interface screen. These steps are carried out serially or sequentially from top to bottom and include therapy mode selection, panel kit installation, fluid bag installation, flow rate settings and patient connection.

Figure 13A:
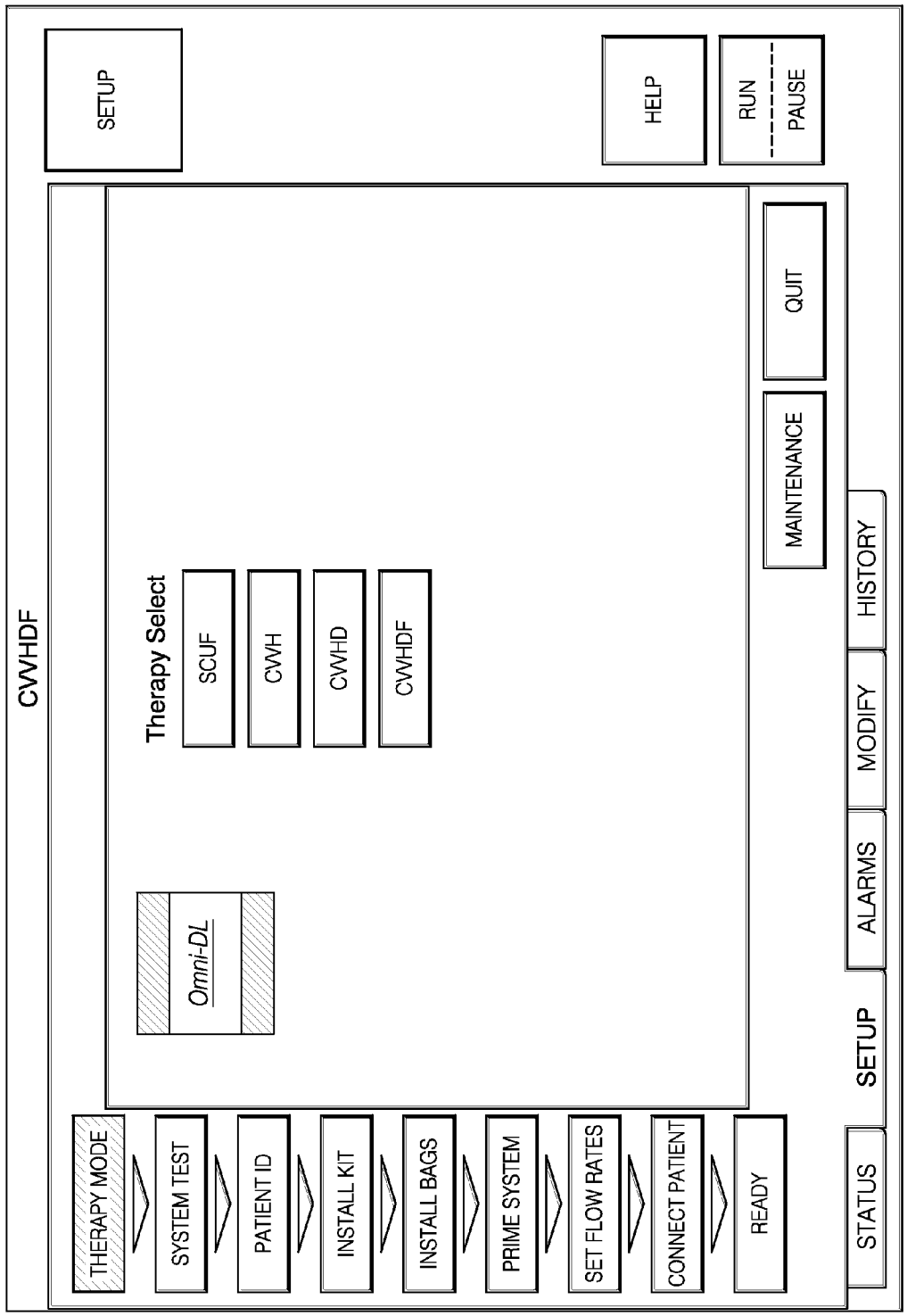
FIGS. 13A-13F and 15A-15C illustrate a number of setup operator interface screens and sequential setup steps.
Figure 13B:
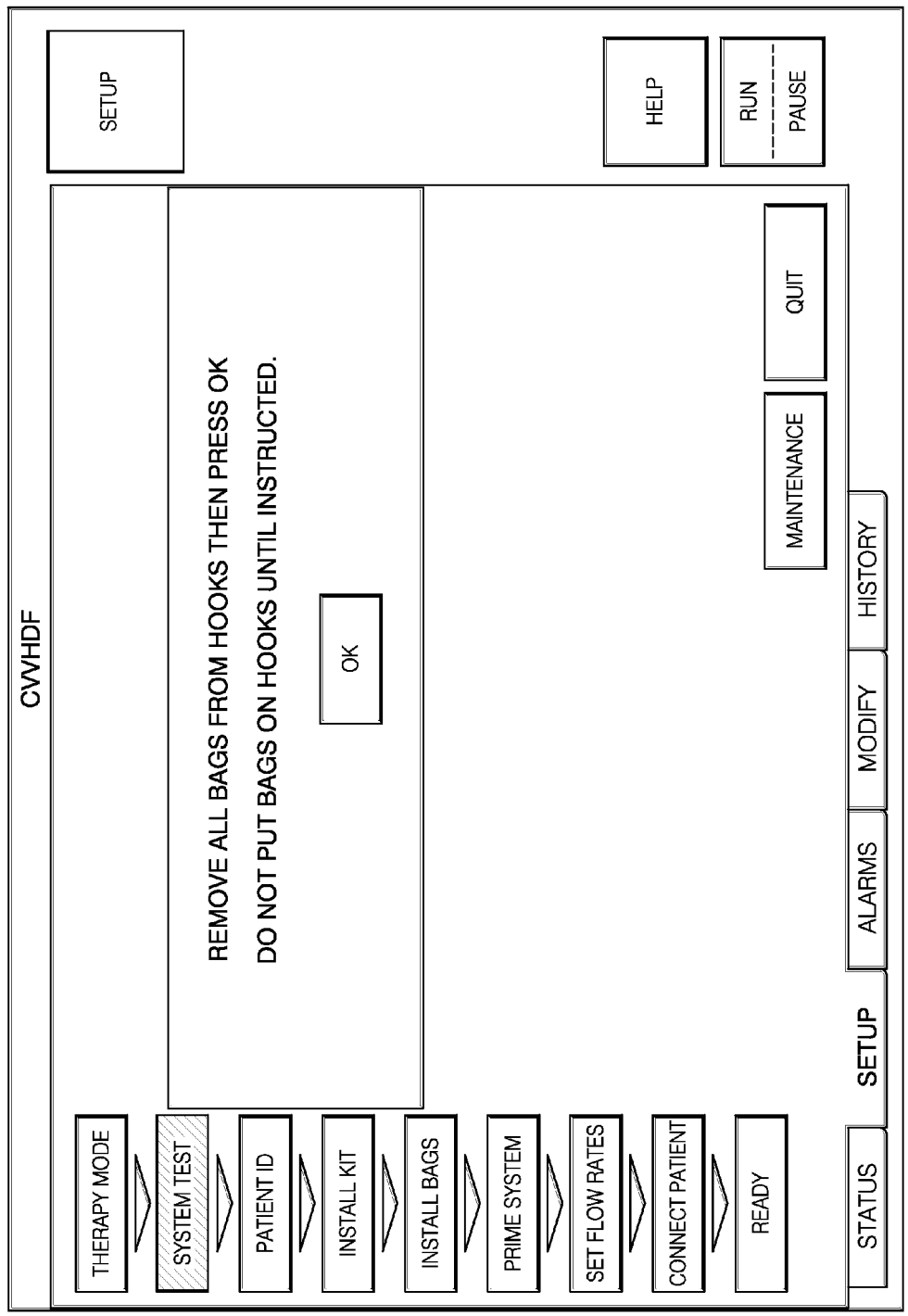
Figure 13C:
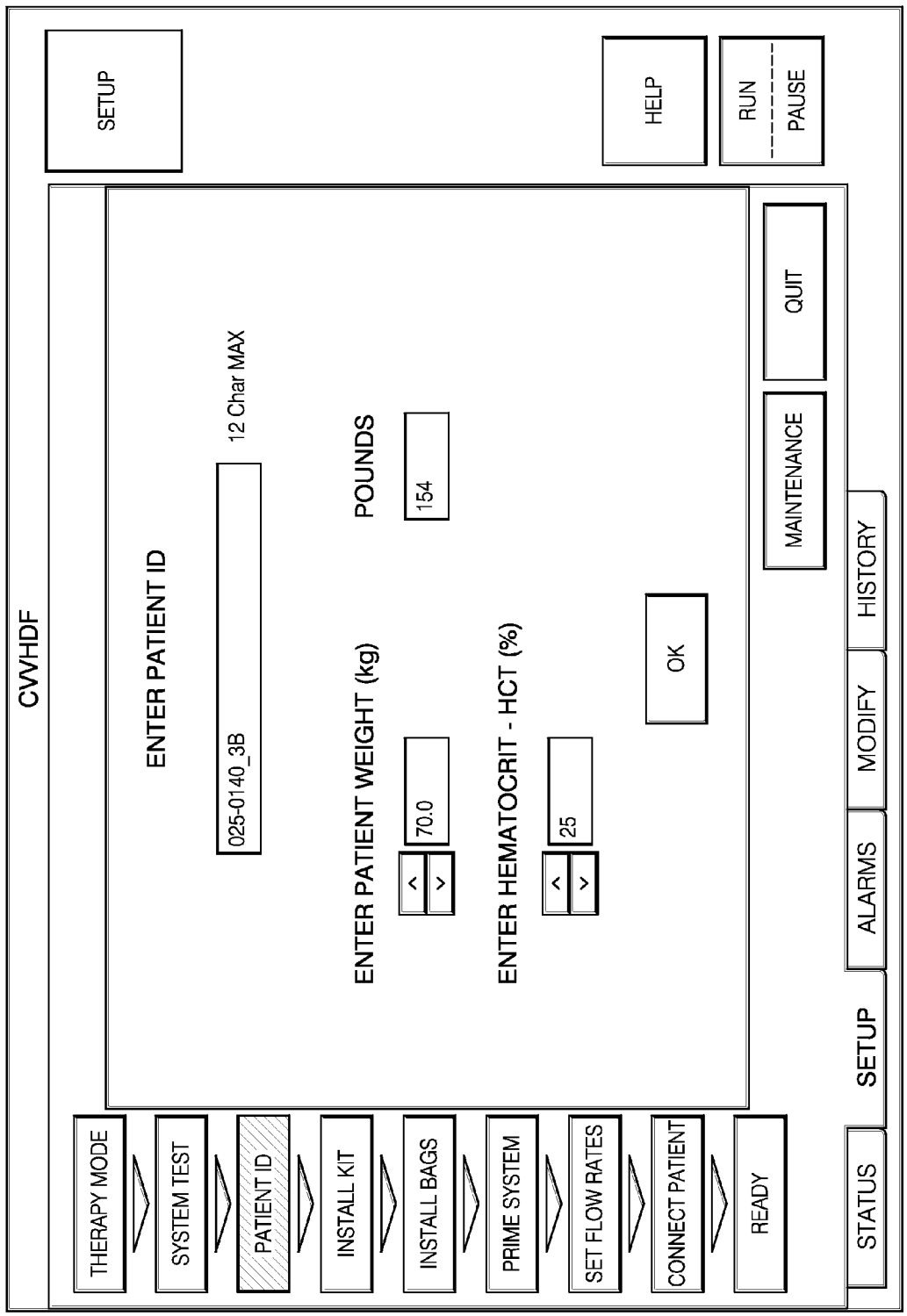
Figure 13D:
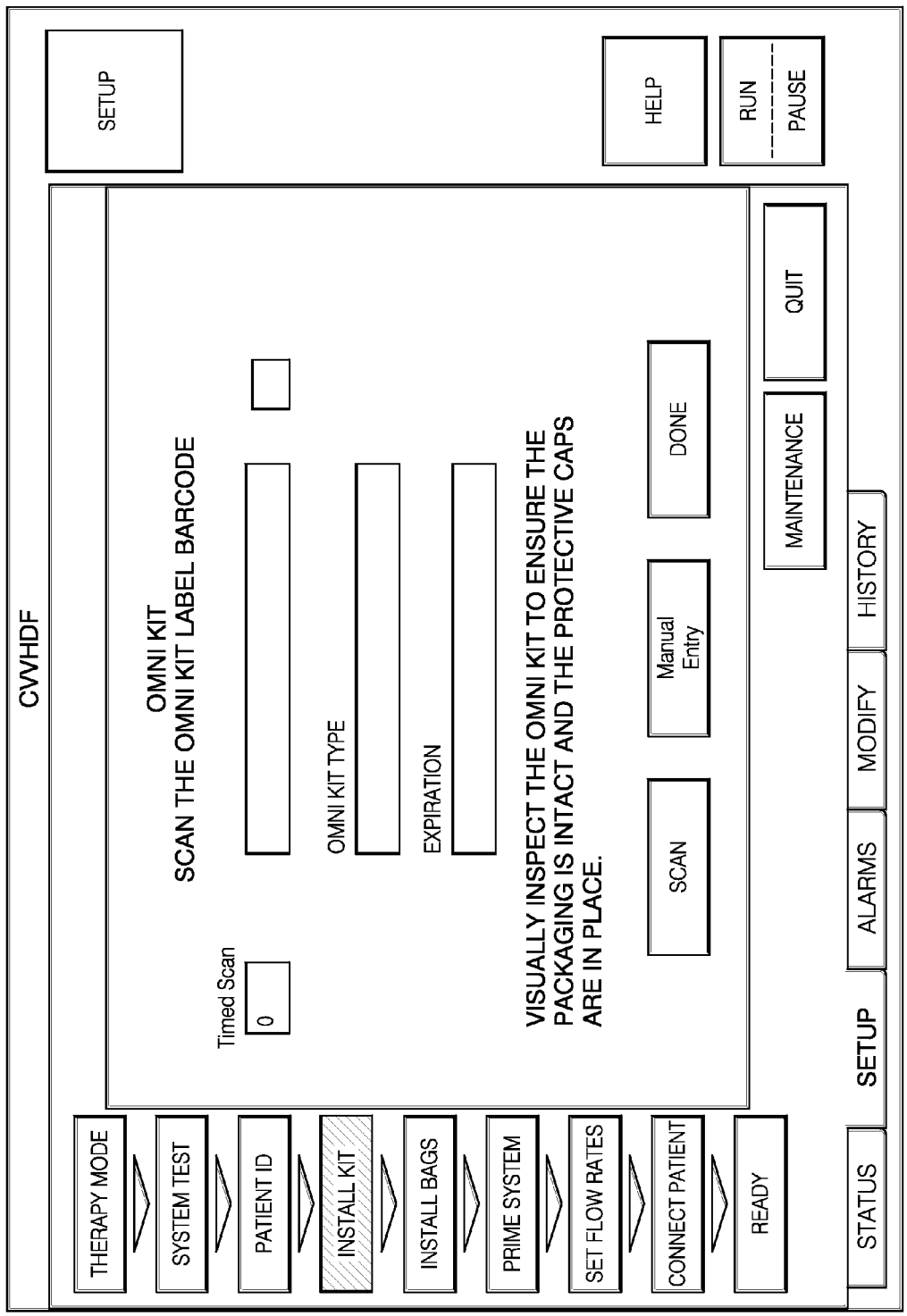
Figure 13E:
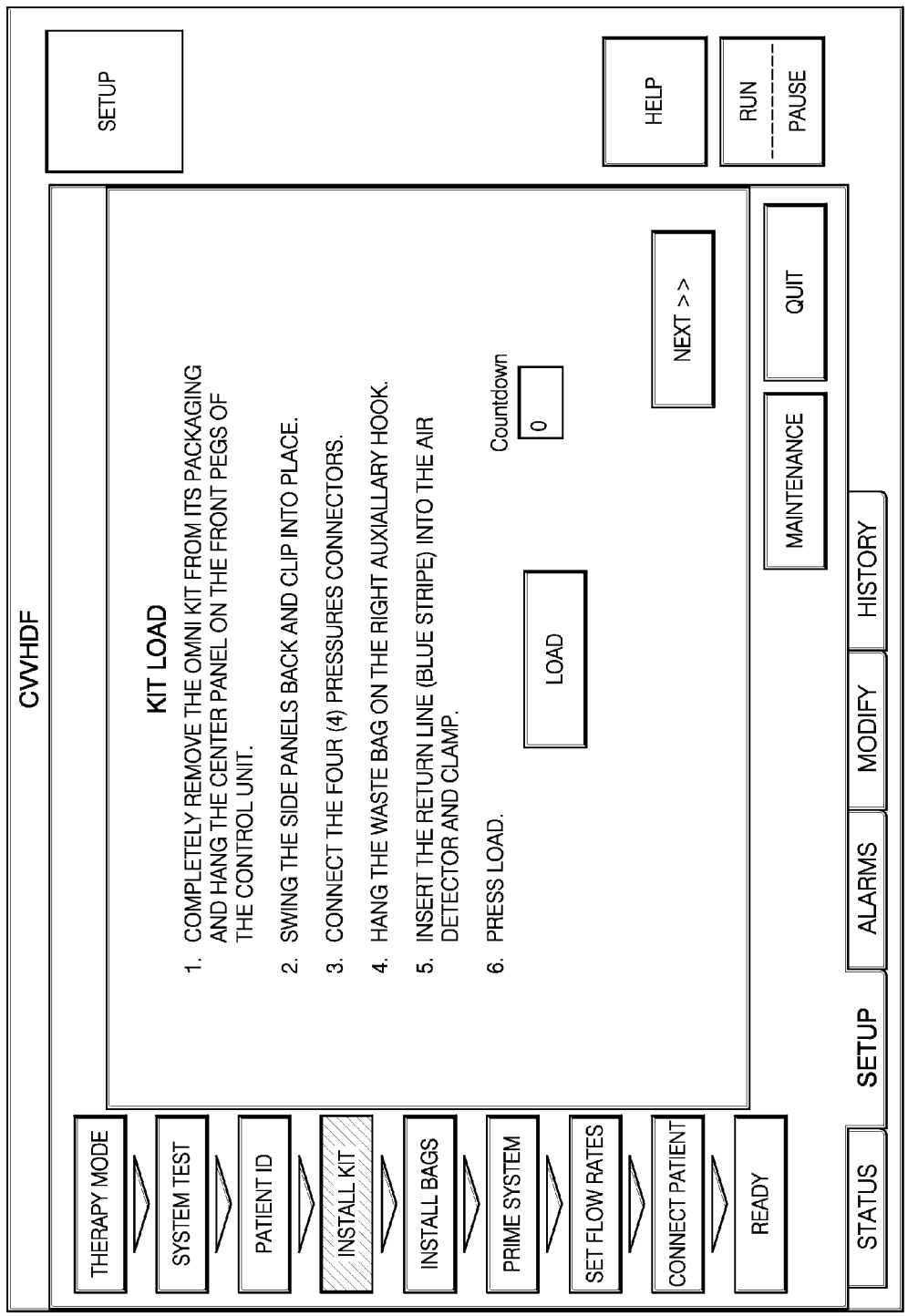

Beginning with the first setup step to be carried out, selection of the therapy mode is shown in FIG. 13A with the operator selecting the therapy desired by touching the appropriate therapy tab. Following the therapy selection, the screen of 13B appears and instructs the operator to ensure that the bag hangers are hanging clear and free of any tubing or bags and the operator presses OK to continue. The next screen shown in FIG. 13C automatically appears for the operator to enter the patient ID, weight and hematocrit, and again pressing OK to continue to the next step of installing the kit with directions to be carried out shown successively in FIGS. 13D and 13E. In one embodiment, the panel kits and the filter cartridges are provided with bar codes and the control unit includes a bar code scanning component for ensuring that the panel kit installed is appropriate for the treatment selected. After scanning the panel kit per FIG. 13D, a new screen, not shown, prompts the operator to scan the filter cartridge to be used during treatment and thereafter press the "Scan" indicator to scan the bar code or enter it manually. The next preparation step for installing and loading the panel kit is instructed as shown in FIG. 13E. The operator will manually mount the side panels and front panel onto the control unit housing and connect the four pressure transducers to the control unit by plugging in the transducer plugs into the correct socket on the control unit. The waste bag (typically a 2L bag) is connected to the fluid effluent line. The specific tubing for connecting the various fluid holding bags may be color coded. Once the panel kit is installed, the operator presses the "Load" tab and the control unit turns the pumps to finish loading the panels including engaging the tubing with the pump rotors.

Figure 13F:
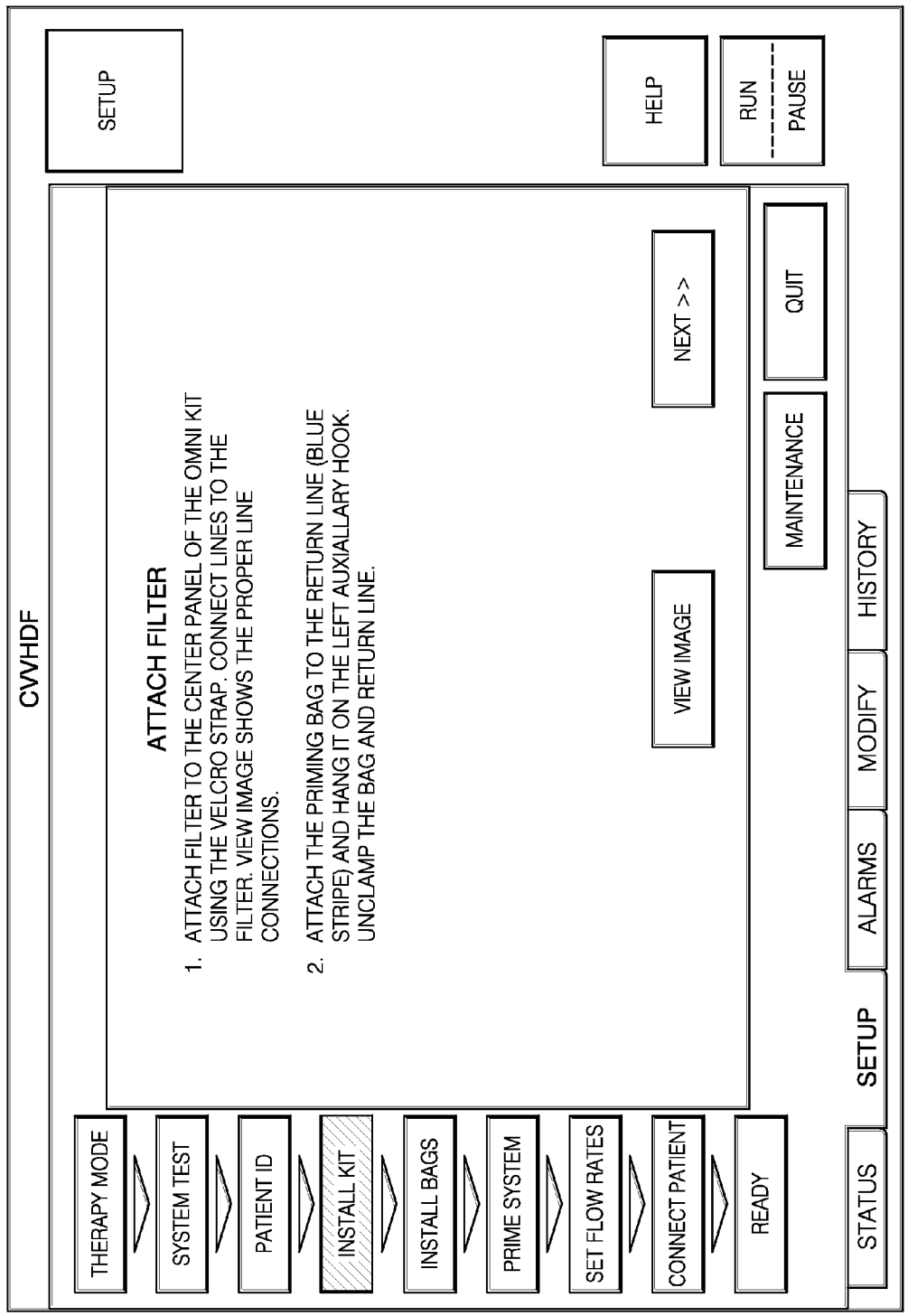

The screen shown in FIG. 13F for the install kit setup step instructs the operator to attach the hemofilter, and connect the fluid tubes (lines) to the filter. Depending on the selected therapy, replacement fluid and dialysate lines will be connected and thereafter the necessary fluid holding bags, effluent bag, replacement fluid bag and dialysate bag will be hung. The bags are hung on the bag hangers (see FIGS. 1 and 2), with the tubing attached to the bottom of the bag (see FIG. 3). It is preferable to hang the effluent bag with the tubing entering the top of the bag. In one embodiment, well designed bag hangers shown and described in U.S. Provisional Patent Application No. 61/105,711 filed Oct. 15, 2008 (TRANSVI.027PR) are used, the description of which is incorporated hereby by reference in its entirety.

Figure 14B:
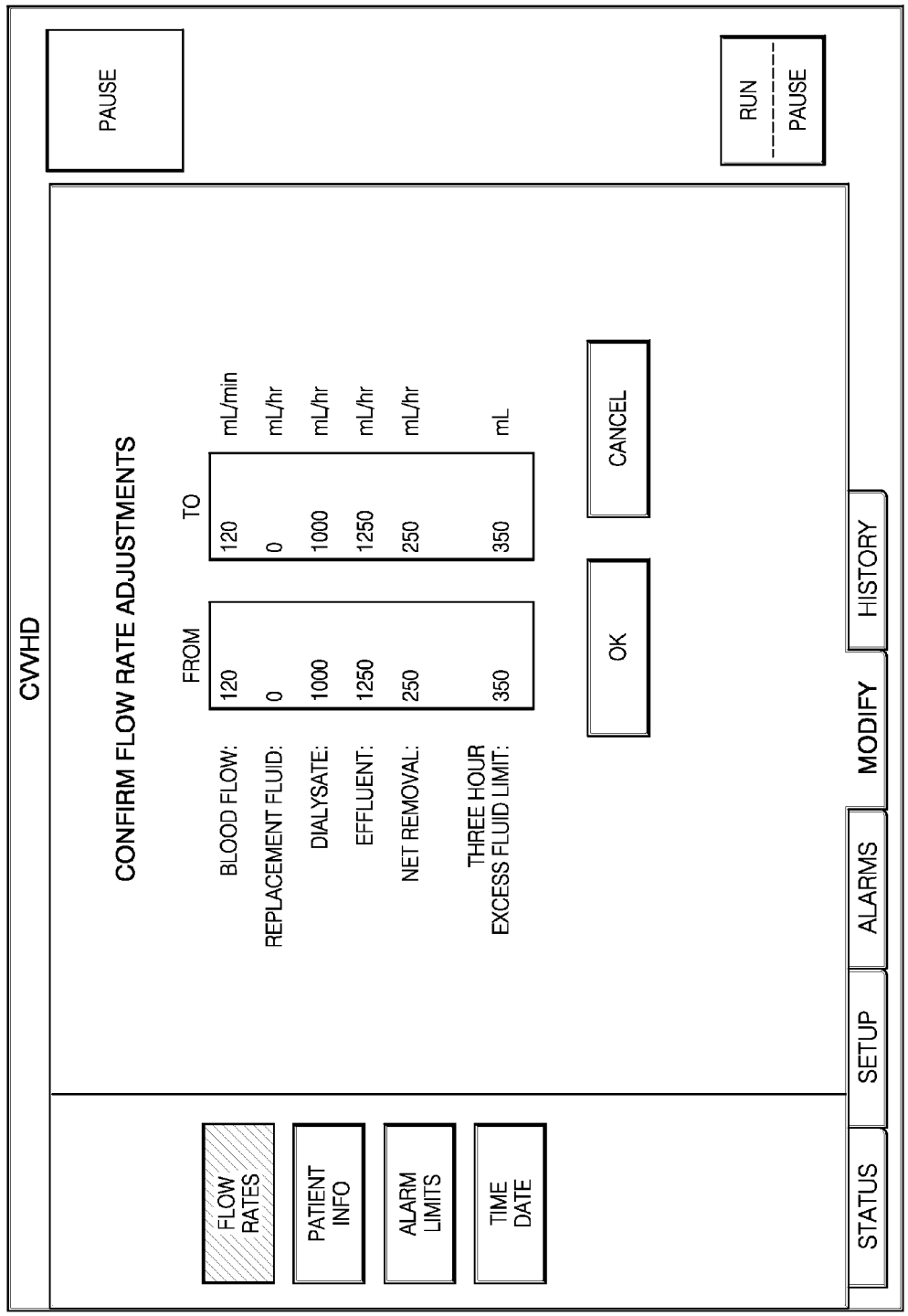
Figure 14C:
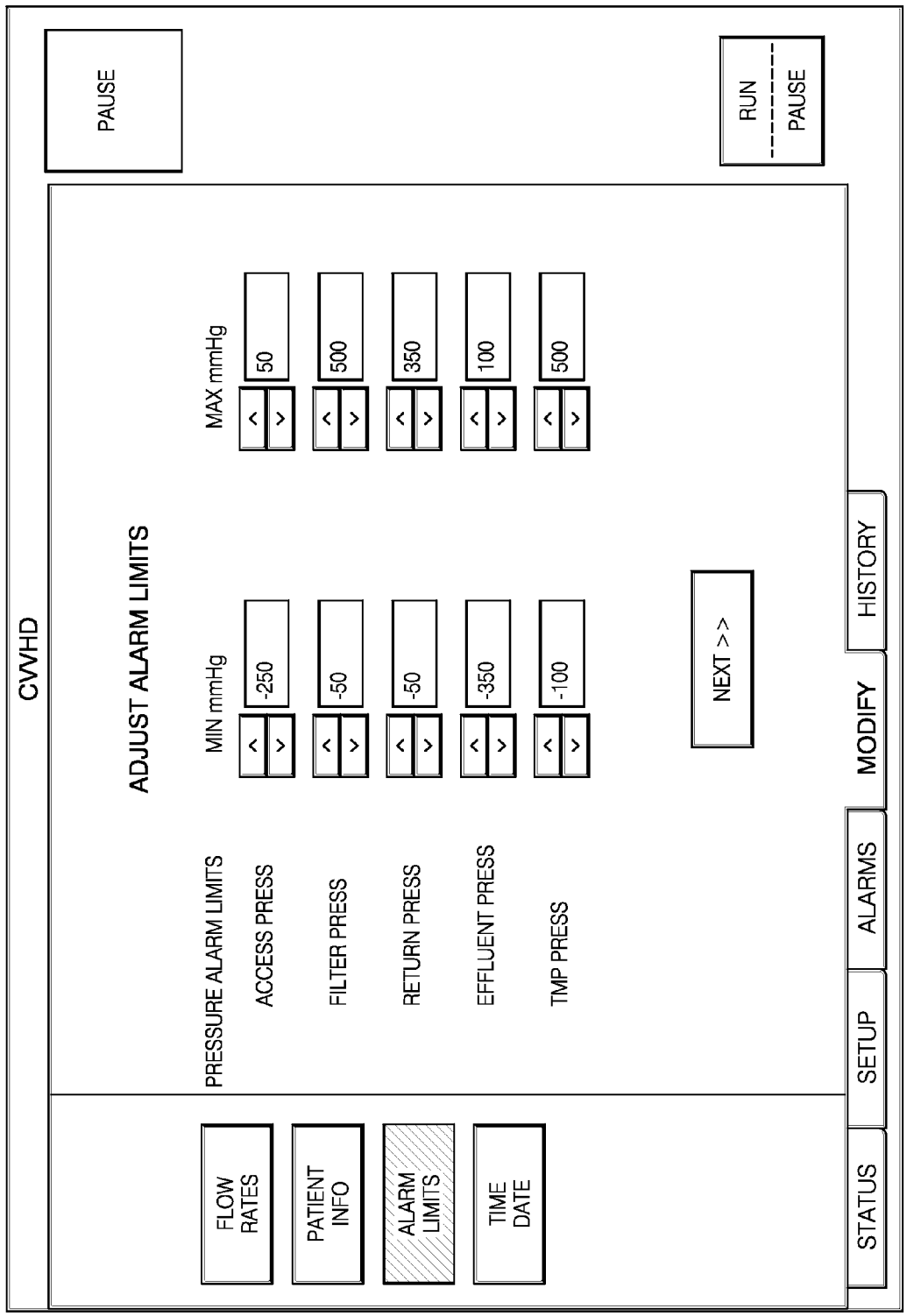
Figure 15A:
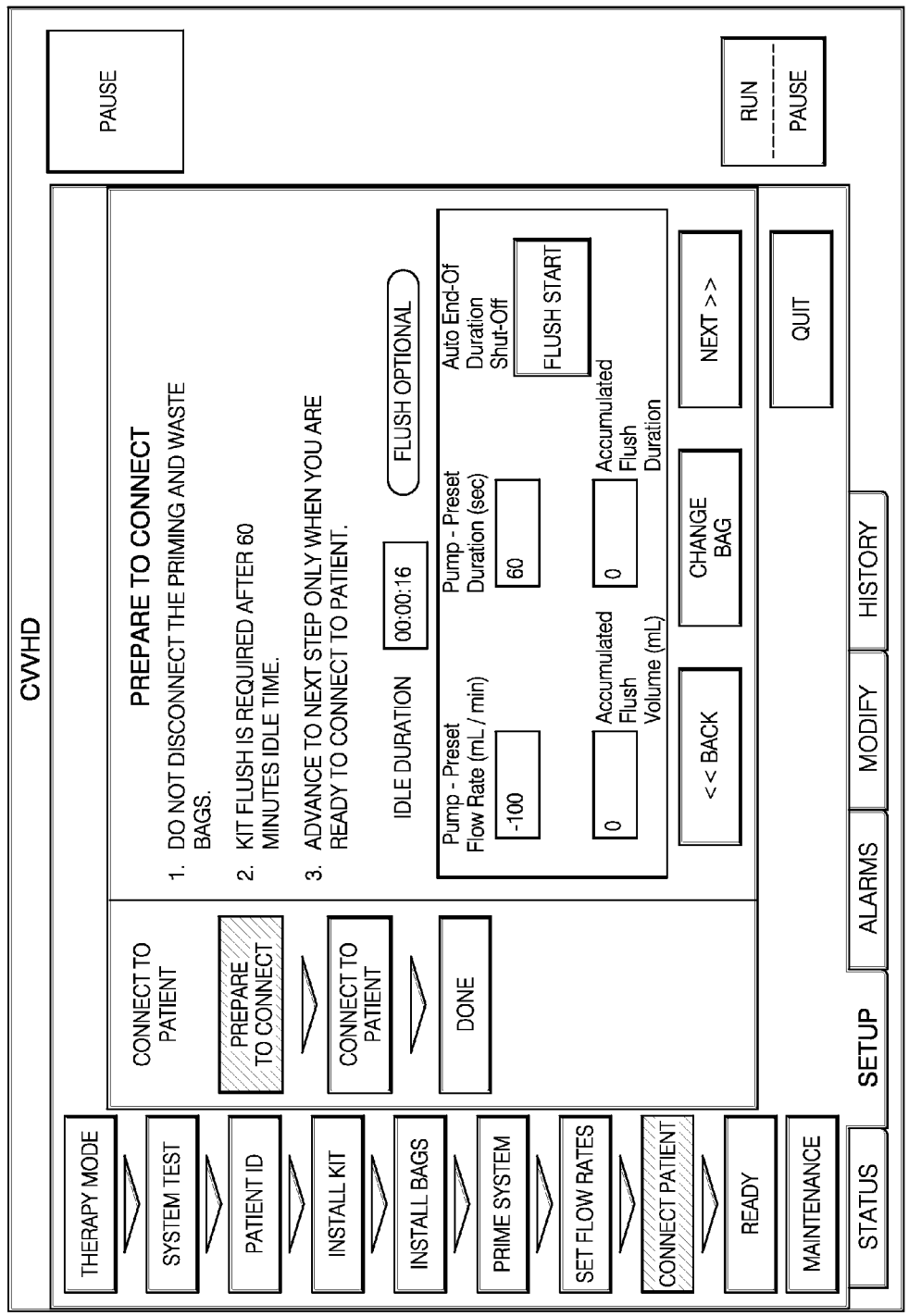
Figure 15B:
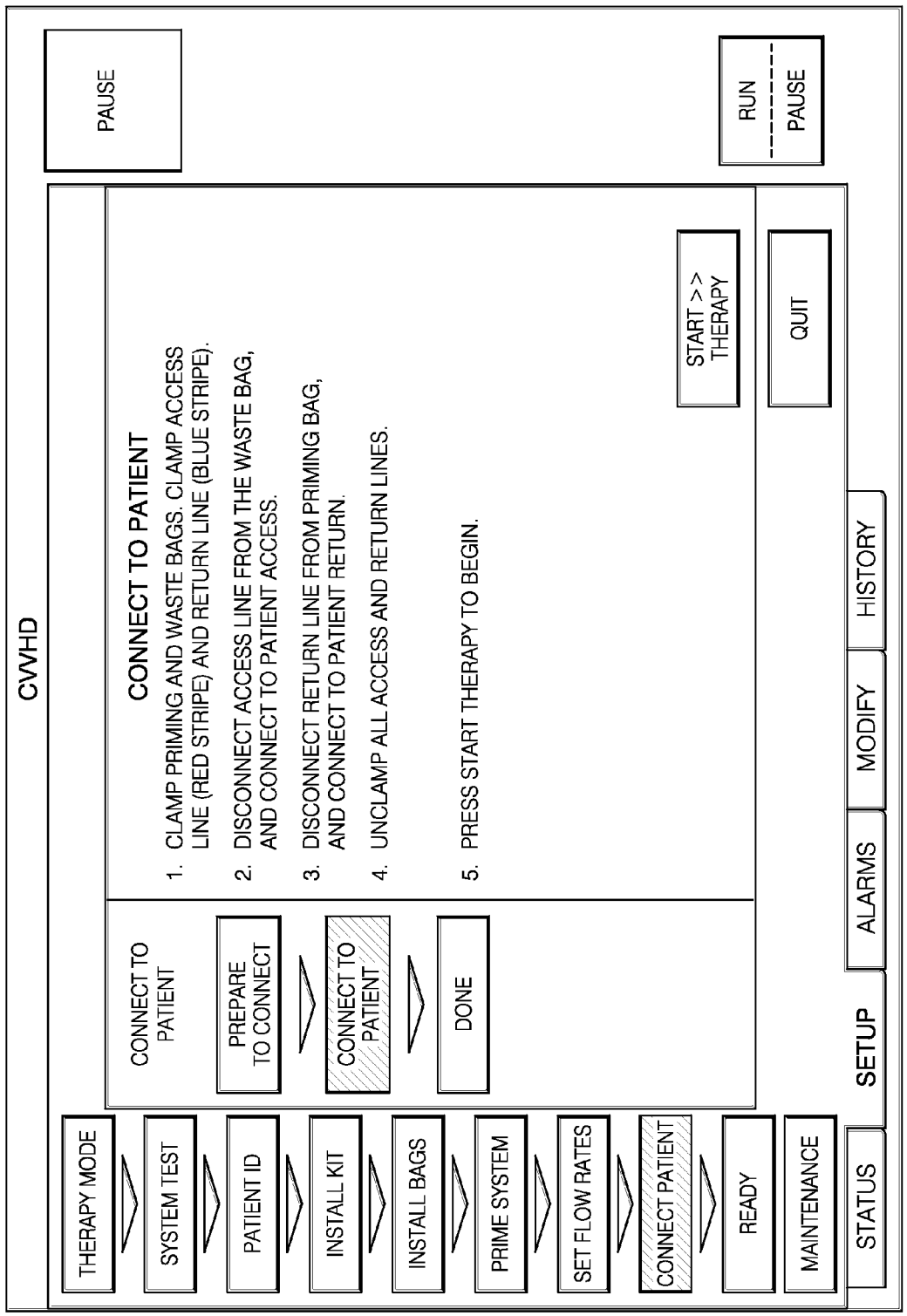
Figure 15C:
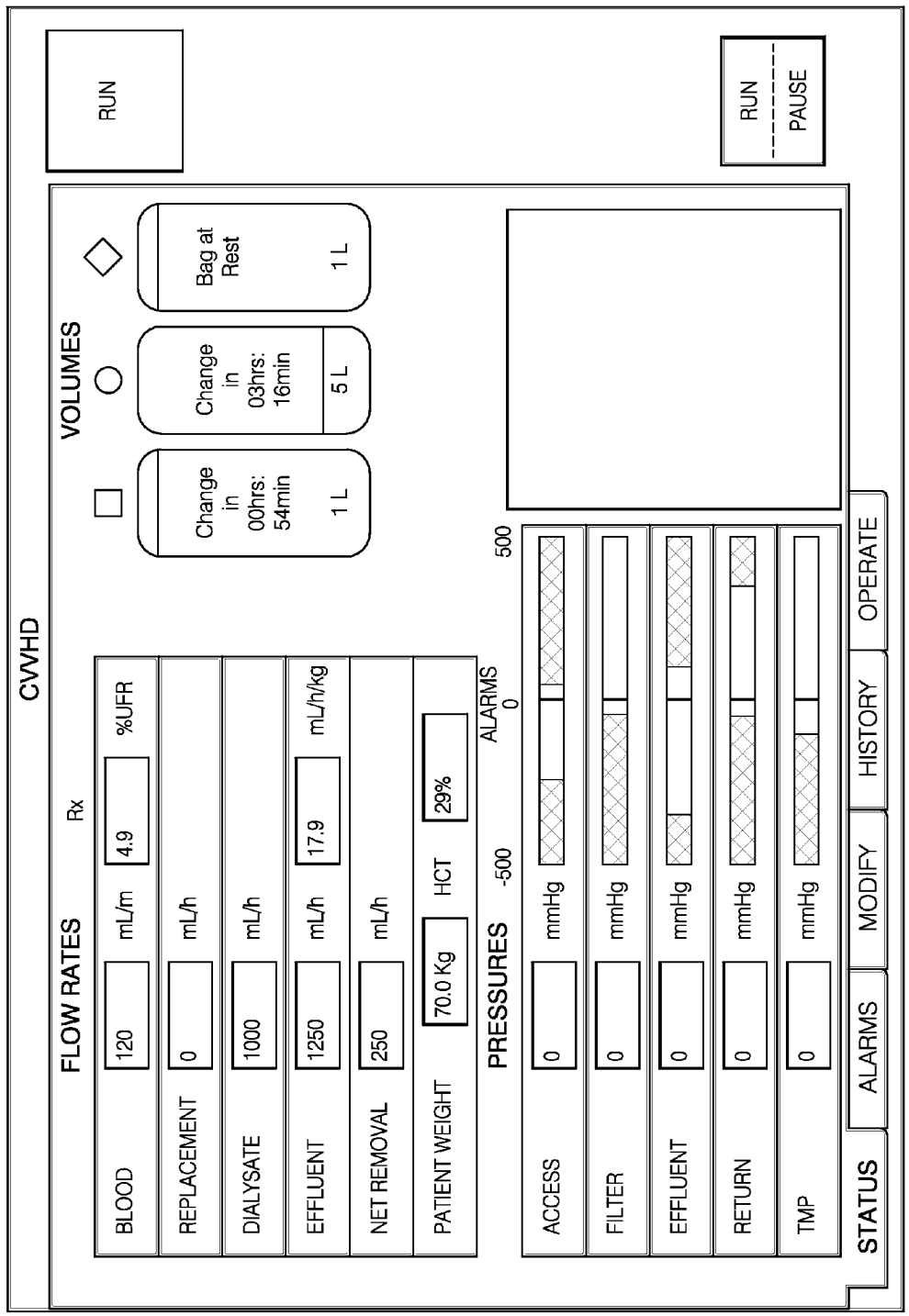

Although not specifically shown, the screens automatically and sequentially appear following bag installation and are for carrying out tasks for priming the system, setting flow rates, setting alarms and connecting a patient to the apparatus. The flow rate settings are accomplished on a setup screen shown in FIG. 14A that automatically appears following completion of the prime system setup step. The operator enters the desired flow rates, touches "Enter," and confirms the flow rates per the screen shown in FIG. 14B. In one embodiment alarm limits may also be confirmed or adjusted per FIG. 14C. Following the aforesaid steps, the operator interface screen automatically returns to the connect patient setup screens shown in FIGS. 15A and 15B, and when patient connection is completed, the control unit enters run mode when the operator presses the "Start Therapy" button. In one embodiment, a status screen such as shown in FIG. 15C may be displayed during the entire patient treatment.

As previously disclosed, another feature of the apparatus and system described herein is the ability to change to a different CRRT therapy during a currently running therapy, without changing the panel kit and without changing the hemofilter, if it is compatible for use in the therapy to be selected. In one embodiment, to change therapy during a currently running therapy, the operator touches an appropriate button on the screen that will access a running therapy shutdown, exit therapy, new therapy selection or other indicia or tab that will allow restart of the software (see, for example, FIG. 9A). Such a procedure may require disconnecting the patient during the setup steps as previously described. Again, however, changing the panel kit and filter is not required.

In another embodiment, a different therapy may be run by manipulating the apparatus without requiring a full startup step sequence. For example, if a replacement fluid bag is installed in a SCUF configuration for infusing a dilute anticoagulant, changing from SCUF to CVVHF may be accomplished by increasing replacement fluid infusion to a higher suitable rate. Examples of other running therapy changes include: CVVHF to SCUF or CVVHDF to CVVHD by adjusting the CVVHF replacement fluid flow to zero; CVVHD to CVVHDF by installing a replacement fluid bag and adjusting the replacement fluid flow rate to a suitable therapeutic level. For such changes, the control software may be provided with operator instructions for such apparatus manipulations, replacement fluid bag and tubing installment and connections, etc., as will be understood to those skilled in the art.

In one embodiment, the setup steps shown during the system setup as previously described are identified by different identifiers as the setup steps are carried out. For example, a setup step that has been completed is identified by a first identifier, a setup step being currently carried out is identified by a second different identifier, and each setup step not yet carried out is identified by a third identifier, different from both the first and second identifiers. Such a feature may be accomplished by using different indicia outlining the different setup steps, for example, accomplished setup steps may be framed by solid lines, a currently conducting setup step may be identified by a flashing or intermittent dashed frame, and the setup steps to be accomplished by yet a different frame, or no frame at all. Alternatively, the setup step identifier may be different colors, for example, accomplished setup step or steps having a green background, a current setup step being shown with a yellow background, or a color different from the background color of the completed steps, and the yet to be carried out steps identified by yet a third color, or no color different from the background of the operator screen on which the tasks to be carried out are set forth. Other different identifiers may be used for carrying out such a function.

A setup step embodiment as previously described is characterized by successive steps to be carried out and shown on the operator interface screen substantially throughout the system setup and with successive setup steps and tasks for the respective step being automatically displayed in response to operator acknowledgement of completion of the tasks of the current setup step. In such an embodiment, the operator may concentrate on the tasks shown on the screen for the respective setup step to be completed and so acknowledged, without the operator having to touch a tab or button on the setup screen other than acknowledgement of completion of the tasks shown on the screen.

In summary, the apparatus and system described hereinabove allows the operator to change the therapy, change a panel kit and/or a filter cartridge, change bags, exit, temporarily disconnect and restart, all during a running patient therapy. The interactive operator control system also provides the step-by-step instructions for carrying out the aforesaid procedures. The operator control system is further characterized by automatically serially identifying different setup steps to be carried out by an operator including showing the list of setup steps to be carried out, identifying the setup steps which have been carried out, are currently being carried out, and which have not yet been carried out. The setup step screen also clearly sets forth the tasks to be carried out by the operator for the respective different setup steps and in response to operator acknowledgement of completion of the steps shown on the screen to be carried out, automatically identifies the next setup step and sequential task to be carried out. Although the specific instructions for selecting and carrying out the plasma treatments described regarding FIGS. 7 and 8 are not shown, such operation is within the purview of the system described hereinabove as will be understood to those skilled in the art.

It is also to be understood that the specific text, sequence and content of the operator instructions shown in the drawings and described herein are by way of illustration and example only and the apparatus, systems and operations thereof are not to be limited thereby.

What is claimed is:

1. An apparatus for carrying out a selected fluid management and/or renal replacement patient therapy comprising:
a control unit having a blood pump and a plurality of fluid pumps mounted thereon, the blood pump located on a blood side of the apparatus and the plurality of fluid pumps located on a fluid side of the apparatus, the control unit comprising a controller configured for operating said blood pump and said fluid pumps, and an interactive operator control system including an operator interface screen operatively connected to said controller, said controller including software configured to operate said apparatus in response to operator input selections;
a replaceable panel kit configured to be manually mounted on and removed from said control unit, the replaceable panel kit comprising a filter cartridge panel having a replaceable filter cartridge mounted thereon, a blood panel having blood supply tubing mounted thereon, and a fluid panel having fluid supply tubing mounted thereon, the blood panel and the fluid panel moveably mounted to the filter cartridge panel, the blood panel positioned on the filter cartridge panel to engage the blood supply tubing with the blood pump after mounting the filter cartridge panel to the control unit, and the fluid panel positioned on the filter cartridge panel to engage the fluid supply tubing with the fluid pumps after mounting the filter cartridge panel to the control unit; and
wherein said interactive operator control system is characterized by operator inputs for selectively changing the panel kit, replacing the replaceable filter cartridge, changing a currently running patient therapy, and providing operator instructions for carrying out the aforesaid.

2. An apparatus of claim 1 wherein said patient therapies are selected from SCUF, CVVH, CVVHD and CVVHDF.

3. An apparatus of claim 2 including:
separate fluid bag hanger assemblies cooperating with said control unit for hanging a fluid waste bag, a replacement fluid bag and a dialysate fluid bag, respectively, and wherein said interactive user control system is further characterized by an operator input for selectively changing one or more of said fluid bags during a running patient therapy.

4. An apparatus of claim 2 wherein said interactive user control system comprises an operator interface screen having touch controls for selecting system operations and for providing operator instructions for carrying out selected system operations and patient therapy sessions.

5. An apparatus of claim 4 wherein said operator interface screen comprises a touch control for selectively changing the entire replaceable panel kit including the filter cartridge during a current running patient therapy session.

6. An apparatus of claim 5 wherein said controller software is configured to provide instructions for changing the panel kit and filter cartridge comprising a message displayed on the operator interface screen of sequential steps to be carried out by an operator including returning blood to the patient, disconnecting the panel kit from the control unit, and unloading the panel kit from the control unit.

7. An apparatus of claim 4 wherein said operator interface screen comprises a touch control for selectively changing the filter cartridge without changing the replaceable panel kit during a current running patient therapy session.

8. An apparatus of claim 7 wherein said controller software is configured to provide instructions for changing the filter cartridge without changing the replaceable panel kit in response to operator selection thereof comprising messages displayed on the operator interface screen of sequential steps to be carried out by an operator including returning blood to the patient, disconnecting the filter, priming the panel set tubing and new filter, and reconnecting the patient blood access and blood return lines.

9. An apparatus of claim 4 wherein said operator interface screen comprises a touch control for selecting temporary patient disconnect and later restart procedure during a current running therapy session.

10. An apparatus of claim 9 wherein said controller software is configured to provide instructions for temporarily disconnecting the patient and restart treatment at a later time in response to operator selection thereof comprising messages displayed on the operator interface screen of sequential steps to be carried out by an operator including returning blood to the patient, manipulating the patient return line, recirculating blood in the tubing, flushing the tubing, and reconnecting the patient blood access and blood return lines to patient catheters.

11. An apparatus of claim 4 wherein said operator interface screen comprises a touch control for selecting therapy termination or changing patient therapy during a running therapy session.

12. An apparatus of claim 4 wherein said operator interface screen comprises a touch control for selectively changing a fluid holding bag during a running patient therapy.

13. An apparatus of claim 1 wherein said operator interface screen comprises a touch control for selectively changing the replaceable panel kit, the filter cartridge, changing patient therapy, and changing a fluid holding bag during a running patient therapy and wherein said controller software is configured to provide step-by-step instructions displayed on the operator interface screen for carrying out the aforesaid.

14. An apparatus of claim 1 wherein said controller software is configured to display on the operator interface screen step-by-step instructions to be carried out by an operator for changing the panel kit, replacing the filter cartridge without changing the panel kit and changing to a different patient therapy without changing the panel kit or filter cartridge.

15. An apparatus of claim 1 wherein said operator control system is further characterized by automatically serially identifying different setup steps to be carried out during system setup including therapy mode selection, panel kit installation, fluid bag installation, flow rate settings and patient connection.

16. An apparatus of claim 15 wherein said different setup steps are serially identified and shown on said operator interface screen, and wherein said operator control system displays on said operator interface screen sequential tasks to be carried out by an operator for the current identified setup step shown on said screen.

17. An apparatus of claim 16 wherein each step of said setup steps that has been completed is identified by a first identifier, a setup step being currently carried out is identified by a second identifier, different from said first identifier, and all setup steps not yet carried out are identified by a third identifier, different from said first and second identifiers, respectively.

18. An apparatus of claim 17 wherein sequential tasks to be carried out for a current setup step identified by said second identifier are shown on said operator interface screen until an operator signals said operator control system of completion of said tasks for said current setup step, and in response thereto, said control system automatically displays sequential tasks to be carried out for the next serially identified setup step shown on said screen.

19. The apparatus of claim 16 wherein said operator interface screen shows said sequential tasks to be carried out in one or more successive screen displays, each said display including a touch screen tab or button identifying completion of the tasks shown, and wherein in response to touching said tab or button, the next successive screen display is shown automatically.

20. The apparatus of claim 1, wherein said apparatus further includes a bar scanning component for scanning at least one of the blood panel, the fluid panel, the filter cartridge panel, or the filter cartridge.

21. An apparatus for carrying out a selected fluid management and/or renal replacement patient therapy comprising:
a control unit having a blood pump and a plurality of fluid pumps mounted thereon, the blood pump located on a blood side of the apparatus and the plurality of fluid pumps located on a fluid side of the apparatus,
a manually replaceable panel kit mounted on said control unit, the replaceable panel kit comprising a filter cartridge panel having a replaceable filter cartridge mounted thereon, a blood panel having blood supply tubing mounted thereon, and a fluid panel having fluid supply tubing mounted thereon, the blood panel and the fluid panel moveably mounted to the filter cartridge panel, the blood panel positioned on the filter cartridge panel to engage the blood supply tubing with the blood pump after mounting the filter cartridge panel to the control unit, and the fluid panel positioned on the filter cartridge panel to engage the fluid supply tubing with the fluid pumps after mounting the filter cartridge panel to the control unit,
said control unit including a controller configured for operating said blood pump and said fluid pumps, and an interactive operator control system including an operator interface screen operatively connected to said controller,
said controller including software configured to operate said apparatus in response to operator input selections, provide apparatus operating instructions, and wherein said interactive operator control system is characterized by operator inputs for selecting SCUF, CVVH, CVVHD, CVVHDF, plasmapheresis and therapeutic apheresis, and
during a currently running patient therapy, selectively changing the replaceable panel kit, replacing the replaceable filter cartridge without changing the panel kit, and changing to a different patient therapy.

22. An apparatus of claim 21 wherein said controller software is configured to display on the operator interface screen step-by-step instructions to be carried out by an operator for changing the panel kit, replacing the filter cartridge without changing the panel kit and changing to a different patient therapy without changing the panel kit or filter cartridge.

23. An apparatus of claim 22 including separate fluid bag hangers cooperating with said control unit and a plurality of fluid holding bags communicating with said fluid tubing, and wherein said interactive user control system is further characterized by providing step-by-step operator instructions for changing a fluid holding bag during a running patient therapy.

24. An apparatus for carrying out a selected fluid management and/or renal replacement patient therapy comprising:
a control unit having a blood pump and a plurality of fluid pumps mounted thereon, the blood pump located on a blood side of the apparatus and the plurality of fluid pumps located on a fluid side of the apparatus, the control unit comprising a controller configured for operating said blood pump and said fluid pumps, and an interactive operator control system including an operator interface screen operatively connected to said controller, said controller including software configured to operate said apparatus in response to operator input selections;
a replaceable panel kit configured to be manually mounted on and removed from said control unit, the replaceable panel kit comprising a filter cartridge panel having a replaceable filter cartridge mounted thereon, a blood panel having blood supply tubing mounted thereon, and a fluid panel having fluid supply tubing mounted thereon, the blood panel and the fluid panel moveably mounted to the filter cartridge panel, the blood panel positioned on the filter cartridge panel to engage the blood supply tubing with the blood pump after mounting the filter cartridge panel to the control unit, and the fluid panel positioned on the filter cartridge panel to engage the fluid supply tubing with the fluid pumps after mounting the filter cartridge panel to the control unit; and wherein said interactive operator control system is characterized by automatically serially identifying different setup steps to be carried out during system setup including therapy mode selection, panel kit installation, fluid bag installation, flow rate settings and patient connection.

25. An apparatus of claim 24 wherein said different setup steps are serially identified and shown on said operator interface screen, and wherein said operator control system displays on said operator interface screen sequential tasks to be carried out by an operator for the current identified setup step shown on said screen.

26. An apparatus of claim 25 wherein each step of said setup steps that has been completed is identified by a first identifier, a setup step being currently carried out is identified by a second identifier, different from said first identifier, and all setup steps not yet carried out are identified by a third identifier, different from said first and second identifiers, respectively.

27. An apparatus of claim 26 wherein sequential tasks to be carried out for a current setup step and identified by said second identifier are shown on said operator interface screen until an operator signals said operator control system of completion of said tasks for said current setup step, and in response thereto, said control system automatically displays sequential tasks to be carried out for the next serially identified setup step shown on said screen.

28. The apparatus of claim 25 wherein said operator interface screen shows said sequential tasks to be carried out in one or more successive screen displays, each said display including a touch screen tab or button identifying completion of the tasks shown, and wherein in response to touching said tab or button, the next successive screen display is shown automatically.

29. The apparatus of claim 24 wherein said operator interface screen includes a touch tab or button for accessing a system operations screen identifying operator inputs for selectively changing the panel kit, replacing the filter cartridge, changing fluid bags and exiting current therapy and starting a new therapy, during a currently running therapy.

* * * * *